(12) United States Patent
Saeki et al.

(10) Patent No.: US 9,492,485 B2
(45) Date of Patent: Nov. 15, 2016

(54) PLURIPOTENT STEM CELL-DERIVED BROWN ADIPOCYTES, PLURIPOTENT STEM CELL-DERIVED CELL AGGREGATE, METHOD FOR PRODUCING SAME, AND CELL THERAPY AND MEDICAL THERAPY THEREFOR

(75) Inventors: Kumiko Saeki, Tokyo (JP); Akira Yuo, Tokyo (JP); Miwako Nishio, Tokyo (JP); Masako Kawasaki, Tokyo (JP); Koichi Saeki, Ibaraki (JP); Mamoru Hasegawa, Ibaraki (JP)

(73) Assignees: ID Pharma Co., Ltd., Ibaraki (JP); National Center for Global Health and Medicine, Tokyo (JP)

( * ) Notice: Subject to any disclaimer, the term of this patent is extended or adjusted under 35 U.S.C. 154(b) by 109 days.

(21) Appl. No.: 14/113,997

(22) PCT Filed: Apr. 26, 2012

(86) PCT No.: PCT/JP2012/061212
§ 371 (c)(1),
(2), (4) Date: Jan. 27, 2014

(87) PCT Pub. No.: WO2012/147853
PCT Pub. Date: Nov. 1, 2012

(65) Prior Publication Data
US 2014/0140967 A1    May 22, 2014

(30) Foreign Application Priority Data

Apr. 27, 2011 (JP) ................................. 2011-100218
Nov. 30, 2011 (JP) ................................. 2011-262842

(51) Int. Cl.
*A61K 35/28* (2015.01)
*A61K 35/35* (2015.01)
*C12N 5/077* (2010.01)

(52) U.S. Cl.
CPC ............... *A61K 35/35* (2013.01); *A61K 35/28* (2013.01); *C12N 5/0653* (2013.01); *C12N 2501/105* (2013.01); *C12N 2501/155* (2013.01); *C12N 2501/165* (2013.01); *C12N 2501/2306* (2013.01); *C12N 2501/26* (2013.01); *C12N 2506/45* (2013.01)

(58) Field of Classification Search
CPC .................................................... A61K 35/28
See application file for complete search history.

(56) References Cited

U.S. PATENT DOCUMENTS 5,942,435 A * 8/1999 Wheeler ..................... 435/325

OTHER PUBLICATIONS

Xiong et al., (2005, Stem Cells and Development, vol. 14, pp. 671-675).*
Brevini et al., 2010, Theriogenology, vol. 74, pp. 544-550.*
Paris et al., 2010, Theriogenology, vol. 74, pp. 516-524.*
Munoz et al., 2008, Theriogenology, vol. 69, pp. 1159-1164.*

* cited by examiner

*Primary Examiner* — Anoop Singh
*Assistant Examiner* — David A Montanari
(74) *Attorney, Agent, or Firm* — Weisun Rao; Greenberg Traurig, LLP

(57) ABSTRACT

Provided are a method of producing brown adipocytes from pluripotent stem cells, a method of producing cell aggregates as an intermediate product thereof, pluripotent stem cell-derived cell aggregates and pluripotent stem cell-derived brown adipocytes produced by these methods, and cell therapy using the pluripotent stem cell-derived brown adipocytes. In the method of producing brown adipocytes from pluripotent stem cells, cell aggregates are produced from pluripotent stem cells by a method including the step (A), and brown adipocytes are prepared from the cell aggregates by a method including the step (B). The step (A) is a step of producing cell aggregates by non-adhesive culture of pluripotent stem cells in serum-free environment in the presence of a hematopoietic cytokine, and the step (B) is a step of producing brown adipocytes by adhesion culture of the cell aggregates in the presence of a hematopoietic cytokine.

4 Claims, 35 Drawing Sheets

FIG. 6

| Gene Name | | Primer sequence (5'- 3') | Product length (bp) | Annealing temperature (°C) |
|---|---|---|---|---|
| UCP1 | Sense | TCTCTCAGGATCGGCCTCTA | 199 | 55 |
| | Antisense | CCGTGTAGCGAGGTTTGATT | | |
| PRDM16 | Sense | GCGGTCTGTTAGCTTTGGAG | 191 | 55 |
| | Antisense | AGTGTCTTCGGAAAGGGACA | | |
| Cide-A | Sense | CGGAACGTGAAGGCCACCAT | 230 | 55 |
| | Antisense | CCCTATCCACACGTGAACCT | | |
| Cytochrome c | Sense | TCTCTTCCTTGGACCACACC | 249 | 55 |
| | Antisense | CAGCCTCACTGTTGGGGTAT | | |
| Elovl3 | Sense | CACTGGTACCACCACAGCAC | 246 | 55 |
| | Antisense | ATCCTGCCTCCACATGTACG | | |
| Pgc-1α | Sense | GTGAAGACCAGCCTCTTTGC | 247 | 55 |
| | Antisense | AATCCGTCTTCATCCACAGG | | |
| PPARα | Sense | AGCCTCACCCTCTGCAGTTA | 161 | 55 |
| | Antisense | AGGTGGTGGCATCAGTCTTC | | |
| Eva1 | Sense | TGGCATACAGCTCACAGCTC | 247 | 55 |
| | Antisense | AGACACCCGGTCCTTAAACC | | |
| PPARγ | Sense | GACCACTCCCACTCCTTTGA | 173 | 55 |
| | Antisense | GATGCAGGCTCCACTTTGAT | | |
| adiponectin | Sense | CTGGGAGCTTCACAAACAT | 227 | 55 |
| | Antisense | CCACAGCTCTGGGTTTGATT | | |
| resistin | Sense | TCCATGGAAGAAGCCATCA | 209 | 55 |
| | Antisense | TGGCAGTGACATGTGGTCTC | | |

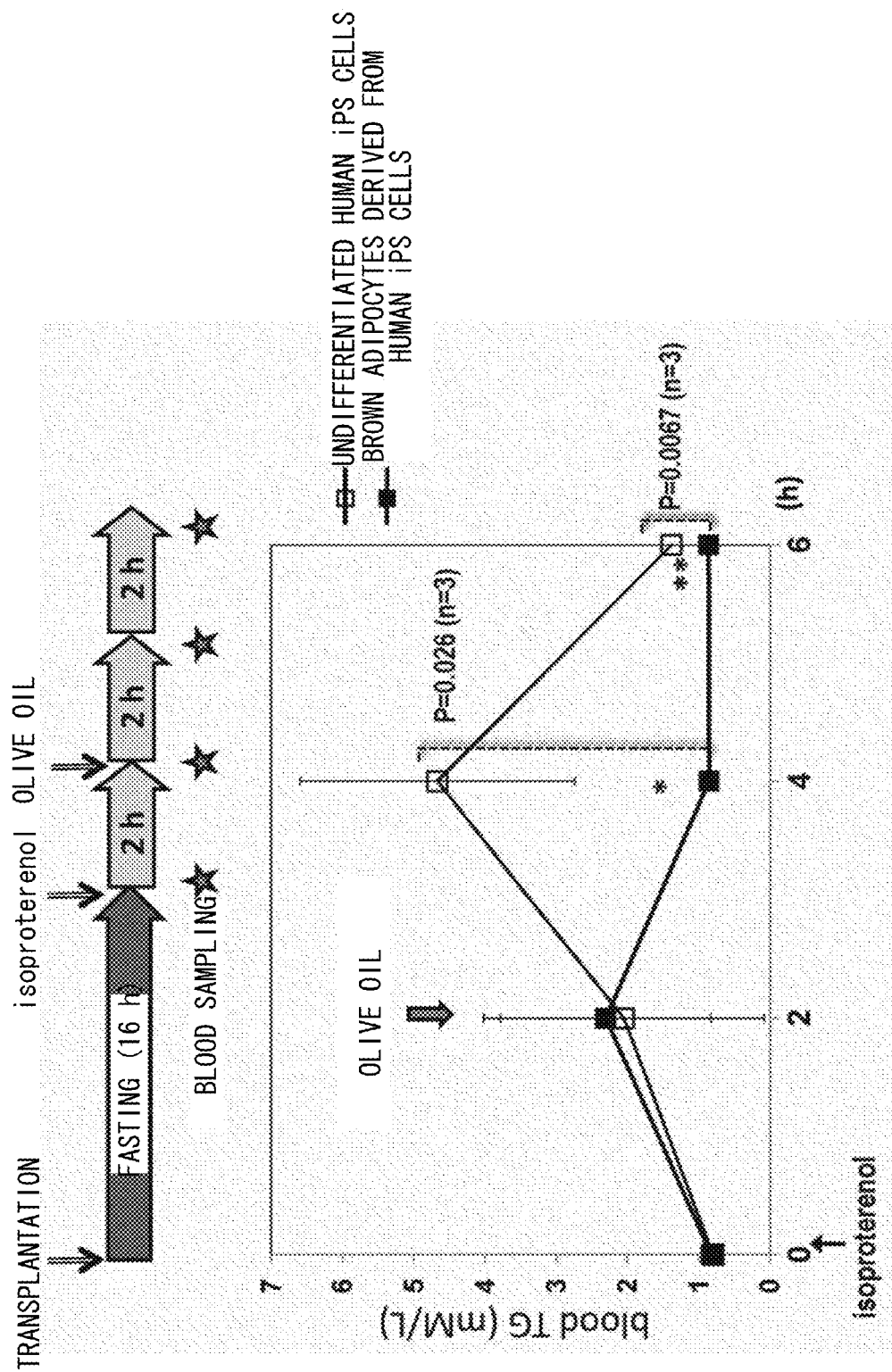

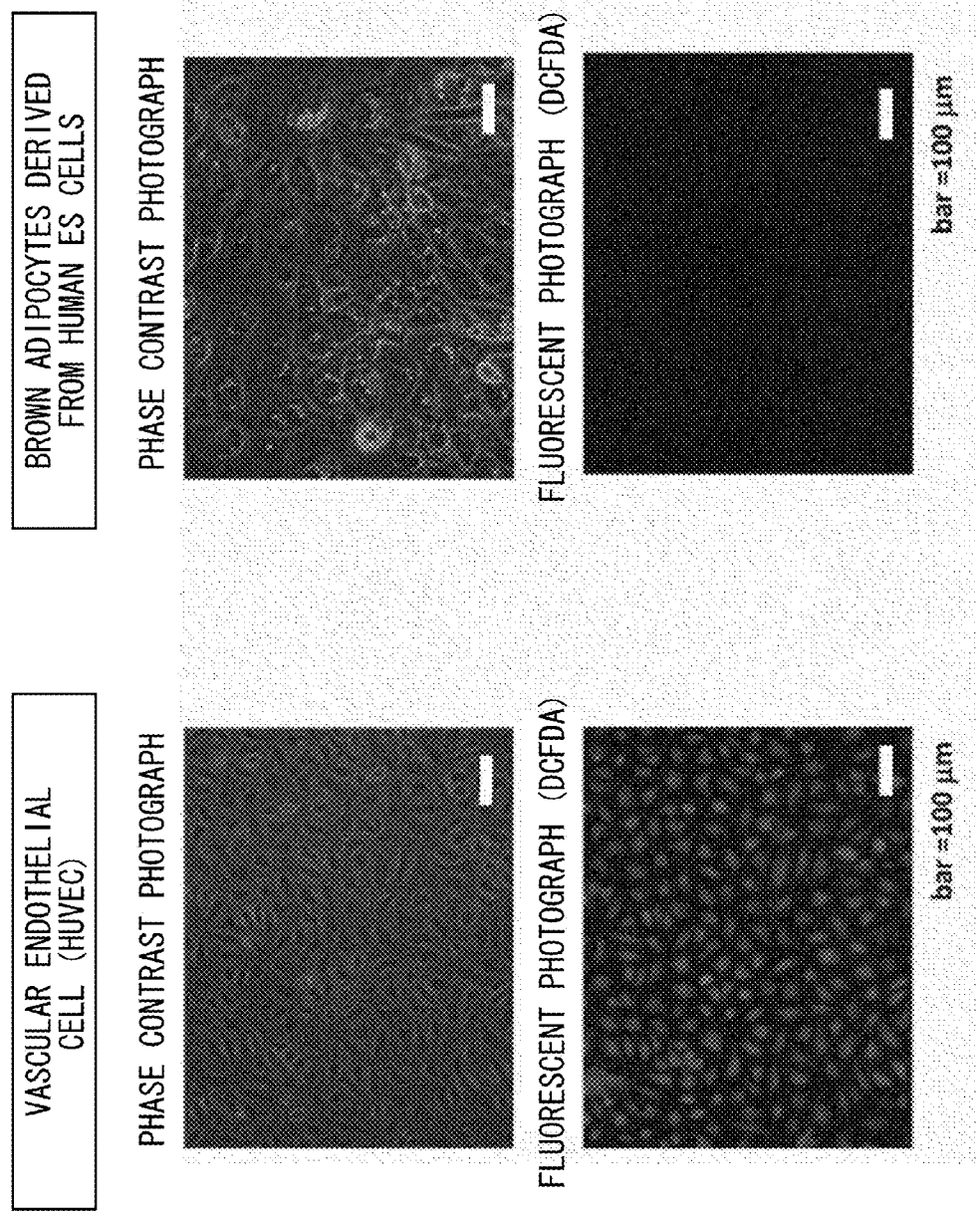

1: UNDIFFERENTIATED ES CELLS
2: BROWN ADIPOCYTES DERIVED FROM HUMAN ES CELLS
3: WHITE ADIPOCYTES DERIVED FROM HUMAN MSC

1: AT 0 h AFTER ADDITION OF ISOPROTERENOL
2: AT 2 h AFTER ADDITION OF ISOPROTERENOL
3: AT 4 h AFTER ADDITION OF ISOPROTERENOL

PLURIPOTENT STEM CELL-DERIVED BROWN ADIPOCYTES, PLURIPOTENT STEM CELL-DERIVED CELL AGGREGATE, METHOD FOR PRODUCING SAME, AND CELL THERAPY AND MEDICAL THERAPY THEREFOR

CROSS-REFERENCE TO RELATED APPLICATIONS

This application is a National Phase application of international Application No. PCT/JP2012/061212, filed Apr. 26, 2012, which claims priority to and the benefit of Japanese Application No. 2011-100218 filed Apr. 27, 2011, and Japanese Application No. 2011-262842 filed Nov. 30, 2011, the contents of all of which applications are incorporated herein by reference in their entireties.

TECHNICAL FIELD

The present invention relates to a method of producing brown adipocytes from pluripotent stem cells, a method of producing cell aggregates as an intermediate product thereof, and pluripotent stem cell-derived cell aggregates and pluripotent stem cell-derived brown adipocytes produced by these methods. The invention also relates to cell therapy and internal therapy using the pluripotent stem cell-derived brown adipocytes.

BACKGROUND ART

In recent years, the number of obese subjects is going on increasing throughout the world. It is no exaggeration to say that "obesity" is a root cause of all lifestyle-related diseases. Various obesity-related diseases (e.g., diabetes mellitus, arteriosclerosis caused by hyperlipidemia or hypertension, and ischemic heart disease or cerebrovascular disorder caused thereby) are the major causes of death in developed countries including Japan. In particular, Japanese people are apt to develop diabetes mellitus even if the degree of obesity is low, compared to Western people, and therefore need a countermeasure against obesity with higher urgency. In emerging countries such as China, Brazil, India, and Russia, the rate of increase in obese subjects is further significant and has become a large social issue.

The basic treatment for obesity is an improvement of lifestyle based on diet therapy and exercise therapy, but it is not easy for obese subjects to reduce weight. The number of obesity patients who cannot obey diet is not small. In addition, it is difficult to perform exercise therapy in many cases due to various diseases associated with obesity (e.g., osteoarthritis, diabetic gangrene, and heart failure).

At the same time, as described by the words "big eater who stays thin", it has been indicated from the past that there is an "important factor" other than excessive eating and lack of exercise as a cause of obesity.

In conventional research on obesity, white adipose tissue (WAT) has been mainly studied.

Recently, it was accidentally revealed in data analysis of nuclear medicine examination (PET/CT) that human also has brown adipose tissue (BAT), which was believed to be present in rodents only (Non-Patent Literature 1). Similar reports have been done successively, and an inverse correlation between the amount of BAT and obesity/onset of metabolic syndrome has been also reported. Today, BAT is recognized as significantly important tissue for assessing the pathological conditions of obesity.

BAT and WAT are also developmentally different from each other. BAT is already formed in the fatal stage, whereas WAT is mainly developed after birth. It is also known that in large mammals including human, the majority of BAT disappears (physiological disappearance) within two days after birth. The mechanism of this is not known at all. The remaining BAT also gradually decreases with aging, of which mechanism is also unknown.

Accordingly, in order to correctly comprehend BAT, it is also important to elucidate the mechanism of the physiological disappearance observed after birth and the disappearance associated with aging. In particular, it should be noticed that small mammals such as mice are not useful for elucidating the mechanism of physiological disappearance.

WAT is an energy storage tissue for storing fat, whereas BAT is an energy production tissue for actively burning fat. The both have absolutely different characteristics in cellular morphology and gene expression.

Morphologically, white adipocytes contain large unilocular lipid droplets and are poor in mitochondria (a small number of mitochondria are present only at the periphery of the nucleus), of which morphology shows segmentation as reflection of a low oxidative phosphorylation activity. On the other hand, brown adipocytes contain small multilocular lipid droplets and are abundant in mitochondria (localizing at the peripheries of the lipid droplets), of which the morphology shows string-like fusion being long lengthwise as reflection of a high oxidative phosphorylation activity and a large number of ladder-type cristae developed intracellularly.

Regarding the gene expression, for example, WAT is characterized by the expressions of resistin and phosphoserine aminotransferase 1 (PSAT1), whereas BAT is characterized by the expressions of elongation of very long chain fatty acids-like 3 (ELOVL3), cell death-inducing DFFA-like effector A (CIDE-A), peroxisome proliferator-activated receptor α (PPARα), peroxisome proliferative activated receptor gamma coactivator 1α (PGC1α), cytochrome C (Cyt-c), epithelial V-like antigen (EVA1), and neurotrophic tyrosine kinase receptor type 3 (NTRK3), in addition to uncoupling protein 1 (UCP1) and PR domain containing 16 (PRDM16), etc.

Among them, UCP1 has an activity of uncoupling the oxidative phosphorylation and ATP production in mitochondria and thereby has an effect of blocking the active oxygen production inevitably associated with oxidative phosphorylation. That is, BAT shows a noteworthy effect of removing oxidative stress concomitant with biological activity through expressing UCP1.

It is also known that WAT and BAT show conflicting physiological effects in vivo. WAT induces oxidative stress by the hypertrophy of cells due to excessive accumulation of fat. As a result, inflammation of adipose tissue is caused to induce insulin resistance at an individual level due to influence of, for example, inflammatory cytokines. However, in BAT, since UCP1 is highly expressed, oxidative stress is not induced, and the insulin sensitivity at an individual level is enhanced.

Thus, BAT has not only an anti-obesity activity but also an activity of improving insulin resistance and is therefore expected to have preventive and therapeutic effects on type 2 diabetes mellitus.

In addition, it has been recently reported that BAT actively uptakes lipids from blood and burns and actively consumes them to show a therapeutic effect on hyperlipidemia (Non-Patent Literature 2).

In a coronary artery bypass surgery, transplantation of WAT of a patient into the surgery site before the surgery improves the results at least in the short term. However, many patients who need coronary artery bypass surgeries have already developed metabolic syndrome. Consequently, vascular restenosis after surgery is concerned in the long term, due to initiation of inflammatory reaction and induction of oxidative stress in the transplanted adipocytes. It is also known that in coronary artery stenosis cases, a large amount of WAT is actually present around the coronary artery.

If BAT, which does not induce oxidative stress, can be transplanted into the site of coronary artery bypass surgery, an improvement in the long-term results can be expected.

Thus, BAT, which is expected to have therapeutic effects on obesity, insulin resistance, type 2 diabetes mellitus, and hyperlipidemia and an effect of improving the result of coronary artery bypass surgery, is significantly important and valuable tissue for complete cure of various diseases associated with metabolic syndrome.

Unfortunately, the occurrence, growth mechanism, functional regulation, and other factors of BAT in human are still unclear in many points. Furthermore, all of adipokines that are known to be involved in metabolic regulation as adipose tissue-derived hormones were identified from WAT, and no "BAT-specific adipokine" that can be expected to show anti-obesity and metabolism-improving activities superior to those of existing adipokines has been identified.

Thus, important findings relating to BAT have not been obtained yet. This is caused by that BAT specimens from normal volunteers are hardly obtained by the following four reasons: 1) in order to identify the positions of BAT, PET/CT inspection, which causes a large quantity of radiation exposure, is necessary; 2) BAT in not all subjects can be visualized by the PET/CT inspection; 3) BAT is scattered in multiple sites (e.g., posterior cervical region and the side of each thoracic vertebra) in the human adult body, and the quantity of BAT is not high (not higher than 300 g in total); and 4) there are no sufficient data for evaluating demerits (e.g., an increase in risk of onset of metabolic syndrome) caused by removal of BAT being such minute tissue.

In order to overcome these problems and supply a sufficient amount of brown adipocytes for the use thereof for research purposes and clinical application (such as cell therapy), it is significantly useful to produce brown adipocytes from pluripotent stem cells having both self-replication ability and pluripotent differentiation ability.

Examples of most generally useful human pluripotent stem cells include human embryonic stem (ES) cells and human induced pluripotent stem (iPS) cells. However, production of brown adipocytes using these human pluripotent stem cells has not been achieved successfully yet.

There are reports on the production of brown adipocytes from somatic stem cells present in mouse bone marrow, skin, and adipose tissue and the production of brown adipocytes from mouse ES cells (Patent Literature 1). However, the in vitro test for confirming the production of brown adipocytes is performed by detecting the expression of message of a UCP1 gene only, and the expressions of other members of the gene cluster (e.g., PRDM16, ELOVL3, CIDE-A, and PPARα) important for expressing the brown adipocyte functions are not investigated. In addition, evaluation from the cellular morphological viewpoints is not performed at all. Accordingly, the quality of the produced brown adipocyte is questionable.

In addition, it is absolutely unclear whether or not this method is applicable to human pluripotent stem cell. Considering that mice have a large amount of BAT and that conversion of WAT into BAT by chronic cold stimulation is frequently observed in mice, it is significantly difficult to believe that the results in mice are directly applicable to human.

Furthermore, as described above, the mechanism of physiological disappearance observed in large mammals including human cannot be elucidated using the mouse stem cell-derived brown adipocytes produced by the above-mentioned method.

There is also a report on that brown adipocytes are produced by culturing preadipocytes collected from mouse BAT or 10T1/2 cell line derived from mouse fetus in a medium containing BMP7 (Non-Patent Literature 3). However, it is absolutely unclear whether or not this method is applicable not only to mouse pluripotent stem cells but also to human pluripotent stem cells.

There is a report on that brown adipocytes were produced by introducing two genes (CCAAT/enhancer binding protein β (C/EBPβ) and PRDM16) into human neonatal fibroblasts (Non-Patent Literature 4). However, considering the lifetime of human fibroblasts, it is difficult to prepare a large amount of brown adipocytes for the purpose of providing a research material or a cell therapy tool. Since these brown adipocytes are forcedly produced by introducing genes, these brown adipocytes are not suitable for use in elucidation of the mechanism of the above-described physiological disappearance.

Accordingly, development of a technology that is applicable to human pluripotent stem cells including human ES cells and human iPS cells and can produce brown adipocytes from pluripotent stem cells without forced induction of differentiation by gene introduction is an urgent need for facilitating basic research on various diseases associated with metabolic syndrome, which is a large social issue in developed countries and emerging countries, and for developing preventive and therapeutic methods.

CITATION LIST

Patent Literature

[Patent Literature 1] Japanese Patent Laid-Open No. 2010-130968
[Patent Literature 2] International Publication No. WO2008/056779

Non-Patent Literature

[Non-Patent Literature 1] Cypess, et al., New England Journal of Medicine, Vol. 360, pp. 1509-1517, 2009
[Non-Patent Literature 2] Bartelt, et al., Nature Medicine, Vol. 17, pp. 200-205, 2011
[Non-Patent Literature 3] Tseng, et al., Nature, Vol. 454, pp. 1000-1004, 2008
[Non-Patent Literature 4] Kajimura, et al., Nature, Vol. 460, pp. 1154-1158,
[Non-Patent Literature 5] Experimental Medicine, Vol. 26, No. 5 (Supplement), pp. 35-40, 2008
[Non-Patent Literature 6] Journal of Cell Physiology, Vol. 9, pp. 335-344, 1977
[Non-Patent Literature 7] Krings, A., et al., Bone, journal homepage: www.elsevier.com/locate/bone, BON-09309, p. 7, 4C, 1st Edition, 2011
[Non-Patent Literature 8] Kushida T, et al., Blood, 97, pp. 3292-9329, 2001

SUMMARY OF INVENTION

Technical Problem

It is a major object of the present invention to provide a technology for stably producing brown adipocytes from pluripotent stem cells without performing gene introduction, in particular, to produce high-quality brown adipocytes from human pluripotent stem cells.

It is also an object of the present invention to provide a technology for stably producing brown adipocytes that can be used for cell therapy of various diseases associated with metabolic syndrome. The brown adipocytes are produced from human pluripotent stem cells in serum-free environment without causing difference among the lines of human pluripotent stem cells.

It is also an object of the present invention to provide a technology for stably producing brown adipocytes that can be a suitable model for occurrence and disappearance (physiological disappearance after birth observed in large mammals and disappearance associated with aging) of brown adipocytes. The brown adipocytes are produced from human pluripotent stem cells in serum-free environment without causing difference among the lines of human pluripotent stem cells.

It is also an object of the present invention to provide a tool for facilitating basic research on human brown adipocytes and for preventing or treating various diseases associated with metabolic syndrome through the provision of a technology for stably producing brown adipocytes that can be used for cell therapy of various diseases associated with metabolic syndrome or can be a suitable model for occurrence and disappearance of brown adipocytes. The brown adipocytes are produced from human pluripotent stem cells established from somatic cells of an arbitrary individual without inserting a foreign gene into the genome, in view of personalized medicine, in serum-free environment without causing difference among the lines.

Solution to Problem

The present inventors further improved the technology (Patent Literature 2) for inducing hematopoietic differentiation of human pluripotent stem cells established by the same group of the inventors (e.g., serum-free culture, variation in composition for reducing the price of cytokine cocktail to be added) and have found during the further improvement that the majority of the cell populations adhering to a culture plate, excluding the hematopoietic cells floating in the medium, have cellular morphology (e.g., multilocular lipid droplets and abundant mitochondria) remarkably similar to that of brown adipocytes. The analysis of gene expression confirmed induction of the expressions of UCP1 and PRDM16, which are genes characteristic to brown adipocytes.

Such an unexpected relationship between hematopoietic cells and brown adipocytes was suggested by the group of Dexter, who established a long-term culture method of hematopoietic stem/precursor cells, in the paper (Non-Patent Literature 6) reporting on morphological characteristics of myelopoietic stromas (cells having a function of supporting hematogenesis). In the paper, bone marrow-derived adherent cells are morphologically classified into three: epithelioid cells, phagocytes, and giant fat cells, and it has been proved that the giant fat cells show hematopoietic stromal activity. As morphological characteristics of the giant fat cells, it is reported that multilocular lipid droplets are abundant and that mitochondria are located on the lipid droplets.

Though such important findings have been reported, the relationship between hematopoietic cells and brown adipocytes has not been studied.

On the other hand, the present inventors were aware of a close relationship between hematopoietic cell differentiation and brown adipocyte differentiation, from the above-described experimental facts and have found that an excellent system for inducing brown adipocyte differentiation can be established by modifying the hematopoietic cell differentiation-inducing system.

The present inventors have optimized the brown adipocyte differentiation-inducing method by modifying the above-mentioned culture technology for inducing differentiation of hematopoietic cells as follows.

Specifically, it was found that the efficiency of producing brown adipocytes is dramatically enhanced by that 1) all steps are performed by using serum-free media; 2) in differentiation-inducing culture composed of two steps, the period of the first step (a suspension culture step for producing cell aggregates) is extended (the culture period of 3 days in the original method is extended to 8 to 10 days); 3) the concentrations of SCF and Flt3L contained in the cytokine cocktail used in the first step are each reduced to about $1/10$ to $1/100$ of the conventional concentrations; and 4) the cytokine cocktail used in the second step (an adhesion culture step of the cell aggregates) contains BMP7 instead of the bone morphogenetic protein 4 (BMP4) in the cytokine cocktail used in the first step.

Based on these findings, the present invention provides the following constituents.

That is, the method of producing pluripotent stem cell-derived brown adipocytes of the present invention is a method of producing brown adipocytes using pluripotent stem cells, wherein cell aggregates are prepared from pluripotent stem cells by a method including the step (A); and brown adipocytes are prepared from the cell aggregates by a method including the step (B):

(A) production of cell aggregates by non-adhesive culture of pluripotent stem cells in serum-free environment in the presence of one or more hematopoietic cytokines; and (B) production of brown adipocytes by adhesion culture of the cell aggregates in the presence of one or more hematopoietic cytokines.

The method of producing pluripotent stem cell-derived cell aggregates of the present invention is a method of producing cell aggregates using pluripotent stem cells, wherein the cell aggregates are prepared from pluripotent stem cells by a method including the step (A):

(A) production of cell aggregates by non-adhesive culture of pluripotent stem cells in serum-free environment in the presence of one or more hematopoietic cytokines.

The method of producing pluripotent stem cell-derived brown adipocytes of the present invention is a method of producing brown adipocytes using pluripotent stem cell-derived cell aggregates, wherein the brown adipocytes are prepared from pluripotent stem cell-derived cell aggregates by a method including the step (B):

(B) production of brown adipocytes by adhesion culture of cell aggregates in the presence of one or more hematopoietic cytokines.

Examples of the hematopoietic cytokine used in the step (A) include BMP4, VEGF, SCF, Flt3L, IL6, and IGF2. In particular, BMP4 is preferred.

The cytokines may be used alone, such as the use of BMP4 only, but a mixture of three or more cytokines is preferably used. A mixture of all of six cytokines is more preferably used.

The cytokines are used, for example, in the following concentrations: BMP4 at 1 to 50 ng/mL, preferably, 10 to 30 ng/mL; VEGF at 0.5 to 20 ng/mL, preferably, 1 to 10 ng/mL; SCF at 1 to 50 ng/mL, preferably, 10 to 30 ng/mL; Flt3L at 0.5 to 20 ng/mL, preferably, 1 to 5 ng/mL; IL6 at 0.5 to 20 ng/mL, preferably, 1 to 5 ng/mL; and IGF2 at 0.5 to 20 ng/mL, preferably, 1 to 10 ng/mL.

Examples of the hematopoietic cytokine used in the step (B) include BMP7, VEGF, SCF, Flt3L, IL6, and IGF2. In particular, BMP7 is preferred.

The cytokines may be used alone, such as the use of BMP7 only, but a mixture of three or more cytokines is preferably used. A mixture of all of six cytokines is more preferably used.

The cytokines are used, for example, in the following concentrations: BMP7 at 1 to 50 ng/mL, preferably, 5 to 20 ng/mL; VEGF at 0.5 to 20 ng/mL, preferably, 1 to 10 ng/mL; SCF at 1 to 50 ng/mL, preferably, 10 to 30 ng/mL; Flt3L at 0.5 to 20 ng/mL, preferably, 1 to 5 ng/mL; IL6 at 0.5 to 20 ng/mL, preferably, 1 to 5 ng/mL; and IGF2 at 0.5 to 20 ng/mL, preferably, 1 to 10 ng/mL.

The non-adhesive culture in the step (A) is carried out, for example, using a common low-adhesive culture plate or a semi-solid medium in such a manner that a state of cells floating in the medium without adhering to the bottom of the culture plate is maintained in a culture apparatus (e.g., in a 5% $CO_2$ incubator at 37° C.).

The adhesion culture in the step (B) is carried out, for example, using a common cell culture container by seeding directly on the container or on a coat (e.g., 0.1% protein such as porcine-derived gelatin) formed on the container (in, for example, a 5% $CO_2$ incubator at 37° C.).

The serum-free environment means a medium for culture not containing any serum such as fetal calf serum but containing a protein ingredient, such as insulin, transferrin, or albumin, or a serum replacement (e.g., GIBCO PFHM-II Protein-Free Hybridoma Medium (registered trademark), Life Technologies, Inc.).

The cell aggregates are spherical (or amorphous) cell agglomerates formed by culturing, for example, pluripotent stem cells in a state of floating in a medium and may have any size and tissue structure and may be linked to one another.

The pluripotent stem cells may be ES cells or iPS cells.

The iPS cells may be iPS cells established by a Sendai virus vector.

The pluripotent stem cells may be human pluripotent stem cells.

The pluripotent stem cell-derived brown adipocytes of the present invention are brown adipocytes produced using pluripotent stem cells and are prepared by a method including the steps (A) and (B):

(A) production of cell aggregates by non-adhesive culture of pluripotent stem cells in serum-free environment in the presence of one or more hematopoietic cytokines; and (B) production of brown adipocytes by adhesion culture of the cell aggregates in the presence of one or more hematopoietic cytokines.

The pluripotent stem cell-derived cell aggregates of the present invention are produced using pluripotent stem cells and are prepared from pluripotent stem cells by a method including the step (A):

(A) production of cell aggregates by non-adhesive culture of pluripotent stem cells in serum-free environment in the presence of one or more hematopoietic cytokines.

The pluripotent stem cell-derived brown adipocytes of the present invention are produced using pluripotent stem cell-derived cell aggregates and are prepared from the cell aggregates by a method including the step (B):

(B) production of brown adipocytes by adhesion culture of cell aggregates in the presence of one or more hematopoietic cytokines.

Furthermore, the pluripotent stem cell-derived brown adipocytes of the present invention are produced using pluripotent stem cells, and the brown adipocytes have induced expressions of at least UCP1, PRDM16, PGC1α, Cyt-c, CIDE-A, ELOVL3, PPARα, EVA1, and NTRK3 genes and have multilocular lipid droplets.

The induction of gene expression means that when the product of a reverse transcription polymerase chain reaction (RT-PCR) using predetermined primers is visualized by agarose electrophoresis, a band derived from the message of each gene is detected in differentiation-induced cells, whereas the band is not detected in undifferentiated pluripotent stem cells at all.

The multilocular lipid droplets are a large number of small spherical lipid droplets present in cytoplasm, and the presence thereof can be confirmed by optical microscopic observation or electron microscopic observation. It is a standard that 15 or more lipid droplets are detected in a photograph of a cell cross section containing a nucleus in electron microscopic observation.

The pluripotent stem cell-derived brown adipocytes of the present invention may have string-like mitochondria, fused long lengthwise and containing a large number of ladder-type cristae therein, around the multilocular lipid droplets.

The string-like mitochondria fused long lengthwise and containing a large number of ladder-type cristae therein are mitochondria that are fused to one another in the longitudinal direction to become long just like a string and contain discoid cristae therein spreading so as to be perpendicular to the longitudinal direction of the mitochondria from wall to wall of the inner membrane and to be densely arranged in parallel to each other.

The pluripotent stem cells may be ES cells or iPS cells.

The pluripotent stem cells may be human pluripotent stem cells.

The cell therapy of the present invention is for preventing or treating obesity and is performed by transplanting the above-mentioned pluripotent stem cell-derived brown adipocytes.

Similarly, the cell therapy of the present invention is for improving insulin resistance or for preventing or treating diabetes mellitus and is performed by transplanting the above-mentioned pluripotent stem cell-derived brown adipocytes.

Similarly, the cell therapy of the present invention is for preventing or treating hyperlipidemia and is performed by transplanting the above-mentioned pluripotent stem cell-derived brown adipocytes.

Similarly, the cell therapy of the present invention is for surgery of producing a coronary artery bypass and is performed by transplanting the above-mentioned pluripotent stem cell-derived brown adipocytes.

Similarly, the cell therapy of the present invention is for facilitating hematogenesis and is performed by transplanting the above-mentioned pluripotent stem cell-derived brown adipocytes.

The internal therapy of the present invention is performed together with any of prevention or treatment of obesity, improvement of insulin resistance, prevention or treatment of diabetes mellitus, prevention or treatment of hyperlipidemia, treatment for facilitating hematogenesis, and surgery of producing a coronary artery bypass. The internal therapy is performed by administrating a material that is secreted by the above-mentioned pluripotent stem cell-derived brown adipocytes.

Advantageous Effects of Invention

The present invention can provide a technology for stably producing brown adipocytes from pluripotent stem cells in serum-free and feeder-free environment.

The present invention can provide brown adipocytes from human pluripotent stem cells, the brown adipocytes having induced expressions of UCP1, PRDM16, PGC1α, Cyt-c, CIDE-A, ELOVL3, PPARα, EVA1, and NTRK3 genes and having multilocular lipid droplets and string-like mitochondria, fused long lengthwise and containing a large number of ladder-type cristae, around the multilocular lipid droplets.

The brown adipocytes produced according to the present invention do not substantially contain cells from different animal species and foreign viral components and are therefore an excellent tool for basic research and also for cell therapy.

BRIEF DESCRIPTION OF DRAWINGS

FIG. 6 is a table showing primers for RT-PCR for detecting brown adipocyte markers.

FIG. 13B is a graph showing changes in blood triglyceride level when brown adipocytes differentiated from human iPS cells (SeV-iPS) were subcutaneously transplanted on the back of mice and an adrenergic β receptor agonist and olive oil were added thereto.

FIG. 15 includes micrographs showing resistance of brown adipocytes differentiated from human ES cells to active oxygen production.

DESCRIPTION OF EMBODIMENTS

Figure 1:
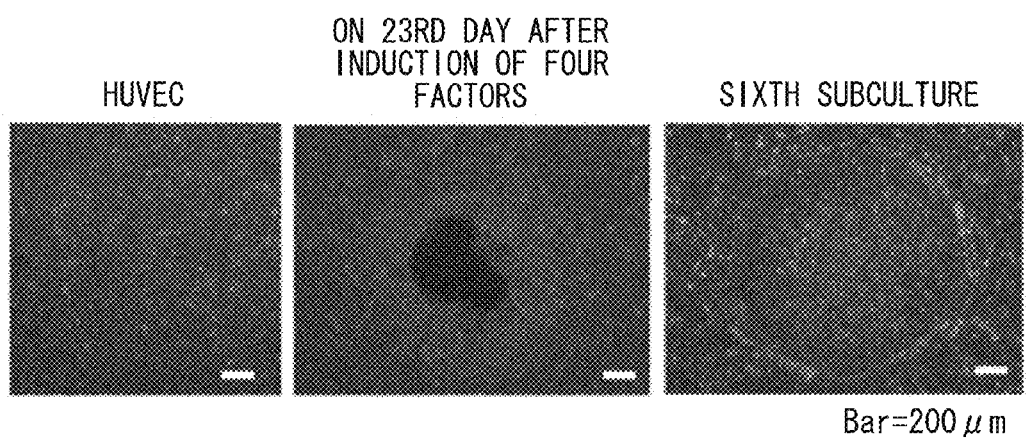
FIG. 1 includes micrographs showing changes in the morphology of a SeV-iPS cell.

Embodiments of the present invention will now be described based on examples shown in figures. Note that embodiments are not limited to the following exemplary examples and can be appropriately designed or modified using conventionally known technologies, such as the above-mentioned documents, within the scope of the gist of the present invention.

The brown adipocytes of the present invention are produced from pluripotent stem cell by a method including the steps (A) and (B):

(A) production of cell aggregates by non-adhesive culture of pluripotent stem cells in serum-free environment in the presence of one or more hematopoietic cytokines: and (B) production of brown adipocytes by adhesion culture of the cell aggregates in the presence of one or more hematopoietic cytokines.

Pluripotent stem cell-derived brown adipocytes are typically prepared from pluripotent stem cells by separating the pluripotent stem cells from feeder cells such as mouse fetal fibroblasts; culturing the pluripotent stem cells in a BMP4-containing medium for producing cell aggregates for about 8 to 10 days in such a manner that a state of cells floating in the medium is maintained in a common low-adhesive culture container; and culturing the resulting cell aggregates in a BMP7-containing medium for brown adipocyte differentiation in a common cell culture container or a common cell culture container coated with a protein component such as gelatin. The production of the pluripotent stem cell-derived brown adipocytes from pluripotent stem cells is achieved during about 10 to 15 days.

Each step will now be described in detail.

(A) Production of cell aggregates by non-adhesive culture of pluripotent stem cells in serum-free environment in the presence of one or more hematopoietic cytokines:

A pluripotent stem cell as the starting material refers to a stem cell having pluripotency, and examples thereof include ES cells, iPS cells, testicular stem cells, adult stem cells, and Muse cells.

The pluripotent stem cells may be human pluripotent stem cells. In such a case, the pluripotent stem cells are derived from a human and form a cell population preserving pluripotent differentiation ability. Examples of the human pluripotent stem cells include human ES cells, human iPS cells, human testicular stem cells, human adult stem cells, and human Muse cells.

The pluripotent stem cells can be acquired or established by known methods. For example, human ES cells can be obtained from domestic establishment institutions (Kyoto University, National Center for Child Health and Development) with permission of the Ministry of Education, Culture, Sports, Science and Technology or can be obtained or purchased from foreign institutions (such as private companies and universities). Human iPS cells can be established by, preferably, a method using a Sendai virus (SeV) vector and are established by, for example, culturing commercially available human fibroblasts in a medium containing a Sendai virus vector carrying a reprogram factor-expressing unit. Examples of the Sendai virus vector carrying a reprogram factor-expressing unit include CytoTune-iPS (manufactured by DNAVEC Corporation). Human iPS cells produced using a retrovirus vector can be purchased from RIKEN BioResource Center or can be obtained from Kyoto University or National Center for Child Health and Development.

In general, cell aggregates can be formed by suspension culture of pluripotent stem cells without using additives necessary for maintaining undifferentiation but using additives having effects of maintaining the viability of the pluripotent stem cells in, for example, a common low-adhesive culture container. The differentiation propensity of the pluripotent stem cell-derived cell aggregates is regulated by the composition of the medium used for producing the cell aggregates.

In order to produce brown adipocytes, the medium for producing cell aggregates must contain at least one hematopoietic cytokine. In other words, in the production of brown adipocytes, the cell aggregates as an intermediate product may have any morphology and any size, but the composition of the medium for producing the cell aggregates must satisfy predetermined requirements. The use of a hematopoietic cytokine at a high concentration (e.g., 100 to 300 ng/mL of SCF or Flt3L) as in hematopoietic differentiation inhibits the production of brown adipocytes and is therefore undesirable.

The basic components of the medium for producing cell aggregates are, for example, a common basic medium, IMDM/F12, and the following additives: 5 mg/mL of bovine serum albumin (BSA), 1% by volume of a synthetic lipid solution (Life Technologies, Inc.), 1% by volume of ×100 insulin-transferrin-selenium (ITS-A) (Life Technologies, Inc.), 450 µM α-monothioglycerol (MTG) (Sigma-Aldrich, Inc.), 2 mM L-Glutamine (Life Technologies, Inc.), 5% by volume of GIBCO PFHM-II Protein-Free Hybridoma Medium (PFHII) (registered trademark) (Life Technologies, Inc.), and 50 µg/mL of ascorbic acid.

Here, as a hematopoietic cytokine, BMP4 (1 to 50 ng/mL, preferably, 10 to 30 ng/mL), VEGF (0.5 to 20 ng/mL, preferably, 1 to 10 ng/mL), SCF (1 to 50 ng/mL, preferably, 10 to 30 ng/mL), Flt3L (0.5 to 20 ng/mL, preferably, 1 to 5 ng/mL), IL6 (0.5 to 20 ng/mL, preferably, 1 to 5 ng/mL), or IGF2 (0.5 to 20 ng/mL, preferably, 1 to 10 ng/mL) is used as an additive.

An example of a hematopoietic cytokine cocktail is composed of BMP4 (20 ng/mL), VEGF (5 ng/mL), SCF (20 ng/mL), Flt3L (2.5 ng/mL), IL6 (2.5 ng/mL), and IGF2 (5 ng/m).

Pluripotent stem cells are cultured in a medium for producing cell aggregates in a common low-adhesive culture container in such a manner that a state of cells floating in the medium without adhering to the bottom of the container is maintained, for example, in a 5% $CO_2$ incubator at 37° C. for 8 to 10 days.

During the culture, for example, a half of the medium is replaced by fresh one every three days. In the replacement of the medium, for example, the low-adhesive culture container is left to stand in a state being tilted by about 30 degrees for about 1 minute to confirm the complete sedimentation of the cell aggregates; a half of only the culture supernatant is gently aspirated off with a pipette; the same amount of a fresh medium for producing cell aggregates is added to the culture container; and then the cell aggregates are uniformly dispersed by lightly shaking the entire low-adhesive culture container.

The low-adhesive culture container used for suspension culture may be any container in which pluripotent stem cells do not adhere to the bottom of the container, and examples of the container include a culture plate coated with 2-methacryloxyethyl phosphorylcholine (MPC) (Thermo Fisher Scientific Inc.) and Hydro cell (registered trademark) (CellSeed Inc.), etc.

In order to separate and remove the feeder cells from the pluripotent stem cells, for example, a suspension of pluripotent stem cells collected by treatment with a dissociation solution is left to stand in a centrifugation tube for about 30 seconds to selectively precipitate only the pluripotent stem cells. The cells are preferably resuspended in a medium for producing cell aggregates and are then suspension cultured in a low-adhesive culture container.

Many of the pluripotent stem cell-derived cell aggregates have a solid spherical shape or a similar shape thereto, but, in some cases, the cell aggregates are amorphous or are fused to one another. In addition, in rare cases, the cell aggregates have a hollow shape. The size of the cell aggregate ranges from a level (diameter: 100 to 300 μm) that can be confirmed with an optical microscope to a level (diameter: 300 to 1000 μm) that are readily visible to the naked eye.

(B) Production of brown adipocytes by adhesion culture of cell aggregates in the presence of one or more hematopoietic cytokines:

The step (B) can be performed by culturing the pluripotent stem cell-derived cell aggregates produced in the step (A) in a common cell culture container. Any cell culture container that is generally used in cell culture can be used.

A common basic medium can be used, and examples thereof include IMDM, IMDM/F12, DMEM, DMEM/F12, and RPMI. Examples of the serum-free culture medium include Esukuron SF-B (EIDIA Co., Ltd.), Esukuron SF-03 (EIDIA Co., Ltd.), ASF-104 (AJINOMOTO CO., Inc.), ASF-104N (AJINOMOTO CO., Inc.), X-VIVO 10 (Lonza group Ltd.), and X-VIVO 15 (Lonza group Ltd.), etc.

Here, as a hematopoietic cytokine, BMP7 (1 to 50 ng/mL, preferably, 5 to 20 ng/mL), VEGF (0.5 to 20 ng/mL, preferably, 1 to 10 ng/mL), SCF (1 to 50 ng/mL, preferably, 10 to 30 ng/mL), Flt3L (0.5 to 20 ng/mL, preferably, 1 to 5 ng/mL), IL6 (0.5 to 20 ng/mL, preferably, 1 to 5 ng/mL), IGF2 (0.5 to 20 ng/mL, preferably, 1 to 10 ng/mL) is used as an additive.

An example of a hematopoietic cytokine cocktail is composed of BMP7 (10 ng/mL), VEGF (5 ng/mL), SCF (20 ng/mL), Flt3L (2.5 ng/mL), IL6 (2.5 ng/mL), and IGF2 (5 ng/m).

The culture conditions for inducing differentiation can be appropriately determined depending on the type of human pluripotent stem cells used and are, for example, at 37° C. in a 5% $CO_2$ incubator for 1 week.

In order to enhance the cell adhesiveness, coating treatment may be performed. The coating treatment can be performed by, for example, putting an aqueous 0.1% porcine gelatin solution in the culture container and leaving it at room temperature for about 10 minutes. A common culture container having enhanced cell adhesiveness (e.g., Corning CellBIND Surface (registered trademark), Corning Inc.) may be used. The medium is preferably replaced by fresh one about every 3 days during the culture period.

Production of pluripotent stem cell-derived brown adipocytes can be confirmed by verification of induced expression of a marker gene of brown adipocytes, such as UCP1, PRDM16, PGC1α, Cyt-c, CIDE-A, ELOVL3, PPARα, EVA1, or NTRK3, by, for example, RT-PCR.

It also can be confirmed by phase contrast microscopic observation of multilocular lipid droplets, electron microscopic observation of multilocular lipid droplets, or observation of mitochondria having ladder-type cristae and fused long lengthwise in cytoplasm.

The function of pluripotent stem cell-derived brown adipocytes can be confirmed through enhanced expression of a gene, such as PRDM16 or UCP1, involved in mitochondria proliferation or heat generation by addition of an adrenergic β receptor agonist such as isoproterenol.

The function of pluripotent stem cell-derived brown adipocytes can be confirmed through an increase in cell temperature or an increase in oxygen consumption when an adrenergic β receptor agonist such as isoproterenol is added to the cells or through an increase in the temperature of the site transplanted with the pluripotent stem cell-derived brown adipocytes when, for example, a mouse is transplanted with the brown adipocytes and administered with an adrenergic β receptor agonist such as isoproterenol.

The thus-prepared brown adipocytes are pluripotent stem cell-derived brown adipocytes and have excellent properties of being substantially free from contamination with cells from different animal species and infection with viruses derived from different animals. The resulting pluripotent stem cell-derived brown adipocytes can be used as a tool for basic research related to occurrence, dedifferentiation, etc. of brown adipocytes and also as a tool for cell therapy of obesity, hyperlipidemia, etc.

The brown adipocytes produced according to the present invention express a gene cluster for exchanging chemical energy stored in triglyceride in lipid droplets into thermal energy.

Accordingly, in vivo transplantation of the brown adipocytes produced according to the present invention into an individual increases the total thermogenesis of the individual to enhance the basal metabolism. Accordingly, an improvement of obesity can be expected in the long term. That is, the brown adipocytes produced according to the present invention are useful as a tool for cell therapy of obesity.

The brown adipocytes produced according to the present invention wastefully consume the chemical energy stored in the body as thermal energy. Consequently, space for storing surplus energy is newly reserved in the adipose tissue.

Consequently, energy due to ingestion of meals is promptly uptaken into the adipose tissue. In other words, the transplantation of the brown adipocytes produced according to the present invention newly reserves a capacity for storing surplus energy and thereby can improve insulin resistance, which is caused by that fat is stored in adipose tissue in an amount larger than the capacity of the adipose tissue, resulting in shortage of reserved capacity for storing surplus energy from ingestion of meals. That is, the brown adipocytes produced according to the present invention are useful as a tool for cell therapy for insulin resistance.

Furthermore, the brown adipocytes produced according to the present invention preserve lipid components uptaken from the outside with the total surface area thereof being large by storing them as multilocular lipid droplets in cytoplasm. In the vicinities of these lipid droplets, a large number of mitochondria showing highly activated oxidative phosphorylation by the electron transport system are present in a form of being fused long in the longitudinal direction and having ladder-type cristae developed intracellularly. Furthermore, the brown adipocytes produced according to the present invention express a gene cluster for exchanging energy due to oxidative phosphorylation into thermal energy.

Consequently, when the brown adipocytes produced according to the present invention is in vivo transplanted, the brown adipocytes show effects of actively uptaking lipid components in blood and burning and consuming them. That is, the brown adipocytes produced according to the present invention are useful as a tool for cell therapy of hyperlipidemia.

The usefulness as a tool for cell therapy of hyperlipidemia can be confirmed by transplanting the brown adipocytes produced according to the present invention into, for example, a mouse having hyperlipidemia induced in advance with high fat diet or the like and monitoring serum fat levels for 1 week. Alternatively, the usefulness can be confirmed by a fasting mouse transplanted with the brown adipocyte produced according to the present invention for a whole day and night, loading the mouse with edible fat and oil such as olive oil through oral administration, and then monitoring the blood triglyceride levels for about 4 hours over time.

The brown adipocytes produced according to the present invention express UCP1. UCP1 causes uncoupling in the electron transport system and thereby shows an activity of blocking the occurrence of active oxygen that is inevitably produced accompanying oxidative phosphorylation in mitochondria. That is, brown adipocytes produced according to the present invention do not produce active oxygen and also do not induce inflammatory reaction.

Accordingly, the occurrence of active oxygen at the transplantation site is prevented in in vivo transplantation of the brown adipocytes produced according to the present invention. This can overcome, for example, a dilemma of fat graft therapy in coronary artery bypass surgery (having a risk that production of active oxygen by transplanted adipocytes induces inflammatory reaction at the revascularized site to make the prognosis of the long-term revascularization poor), resulting in an improvement of a long-term prognosis after revascularization surgery. That is, the brown adipocytes produced according to the present invention are useful as a tool for cell therapy for fat graft therapy in coronary artery bypass surgery.

It is well known that the cells of some adipocyte cell lines derived from mouse bone marrow are "hematopoietic stromal cells" having hematopoiesis supporting ability. As described above, the hematopoietic stromal cells present in mouse bone marrow have morphological characteristics as brown adipocytes. In addition, it has been recently reported that brown adipocytes are present also in mouse bone marrow (Non-Patent Literature 7). At the same time, it is also known that white adipocytes produced from human bone marrow mesenchymal stem cells do not have hematopoiesis supporting ability. That is, it is suggested that brown adipocytes positively control hematogenesis whereas white adipocytes negatively control hematogenesis. Based on these findings, the brown adipocytes produced according to the present invention are believed to be useful as a tool for cell therapy of myelosuppression associated with anticancer treatment and hematopoietic disorder.

In vivo administration of the adipokines secreted by the brown adipocytes produced according to the present invention acts on the liver, skeletal muscle, white adipocytes, and so on to improve the metabolism of lipid and glucose and also indirectly acts on myeloid hematopoietic precursor cells to improve the hematopoietic function. That is, the materials secreted by the brown adipocytes produced according to the present invention are useful as a tool for internal therapy that is performed together with, for example, prevention or treatment of obesity, improvement of insulin resistance, prevention or treatment of diabetes mellitus, prevention or treatment of hyperlipidemia, treatment for facilitating hematogenesis, or surgery of producing a coronary artery bypass.

EXAMPLES

Example 1

Induction of Human Induced Pluripotent Stem Cell Using Sendai Virus Vector

First, $2.5 \times 10^5$/well umbilical vein endothelial cells (HUVEC, Lonza group Ltd.) were seeded on a 6-well culture plate coated with 0.1% pocine gelatin and were cultured in an EGM-2 medium (Lonza group Ltd.) at 37° C. in a 5% $CO_2$ incubator. Subsequently, the cultured cells were infected with the following vectors (a) to (d) in a concentration of MOI=3:

| | |
|---|---|
| SeV18+OCT3/4/TSΔF vector | (a) |
| SeV18+SOX2/TSΔF vector | (b) |
| SeV18+KLF4/TSΔF vector | (c) |
| SeV(HNL)c-MYC/TS15ΔF vector | (d) |

On the following day of the infection with the vectors, the medium was replaced by a 10% FBS-containing DMEM, followed by culture at 37° C. in a 5% $CO_2$ incubator for 6 days. Subsequently, cells transfected with the vectors were detached with Accutase (Innovative Cell Technologies, Inc.) and were cultured on $6.0 \times 10^5$ cells of mouse fetal fibroblasts (MEFs) irradiated with X-ray, which had been prepared on a gelatin-coated 10-cm culture plate, at $9.0 \times 10^5$ to $1.5 \times 10^6$ per 10-cm culture plate. On the following day, the 10% FBS-containing DMEM was replaced by a medium for primate ES cells (ReproCELL Inc.) (containing 5 ng/mL of FGF 2), followed by culture in a 3% $CO_2$ incubator. The medium was replaced every day.

FIG. 1 includes micrographs showing morphological changes in HUVEC-derived human induced pluripotent stem cells (SeV-iPS cells).

Colonies appeared after several days of the culture, and human embryonic stem cell-like colonies appeared by culture for about 20 days. As shown in the photographs of FIG. 1, flat colonies, which were obviously different from HUVEC before the induction, but similar to those observed in human embryonic stem cells, were detected. The human embryonic stem cell-like colonies had the same appearance as those conventionally reported (Non-Patent Literature 5).

These colonies were isolated with a micropipette and were then cultured on a fresh MEF layer. The cells could stably be passaged and expanded by subculture through a dissociation procedure using a human pluripotent stem cell dissociation solution (0.25% trypsin (Life Technologies, Inc.), 1 mg/mL collagenase IV (Wako Pure Chemical Industries, Ltd.), 20% KnockOut (registered trademark) Serum Replacement (Life Technologies, Inc.), and 1 mM $CaCl_2$).

In order to show whether or not the cells prepared by the experiment above expressed markers characteristic to pluripotent stem cells, the following experiment was further performed.

Example 2

Confirmation that Human Induced Pluripotent Stem Cells Established by Using Sendai Virus Vectors were Maintained in an Undifferentiated State Expressions of SSEA4 and OCT3/4, which are markers of undifferentiated human pluripotent stem cells, were investigated with a flow cytometer (FACSCalibur (registered trademark)) (Becton, Dickinson and Company).

Specifically, in the case of SSEA4, the SeV-iPS cells prepared in Example 1 were collected by a treatment with a pluripotent stem cell dissociation solution (0.25% trypsin (Life Technologies, Inc.), 1 mg/mL collagenase IV (Wako Pure Chemical Industries, Ltd.), 20% KnockOut (registered trademark) Serum Replacement (Life Technologies, Inc.), and 1 mM $CaCl_2$) and were dispersed by a treatment with trypsin/EDTA solution (Sigma-Aldrich, Inc.) and then floated in a FACS (registered trademark) buffer (×1 PBS, 0.05% $NaN_3$, 5% FBS). To the suspension, 2% mouse BD Fc Block (Becton, Dickinson and Company) is added and then anti-human SSEA4 phycoerythrin conjugated mouse IgG (R&D Systems Inc.) diluted to 1/10 were added. The mixture was left to stand on ice for 60 minutes. After washing with a FACS (registered trademark) buffer, the expression of SSEA4 was analyzed with a flow cytometer.

In the case of OCT3/4 expression, the collected SeV-iPS cells were subjected to cell fixation and cell membrane permeabilization with FIX & PERM CELL PERMEABILIZATION KIT (Life Technologies, Inc.), and 2% mouse BD Fc Block (Becton, Dickinson and Company) and anti-human OCT3/4 phycoerythrin conjugated rat IgG (R&D systems Inc.) diluted to 1/10 were added thereto. The mixture was left to stand on ice for 60 minutes. After washing with a FACS (registered trademark) buffer, the expression of OCT3/4 was analyzed with a flow cytometer.

Figure 2:
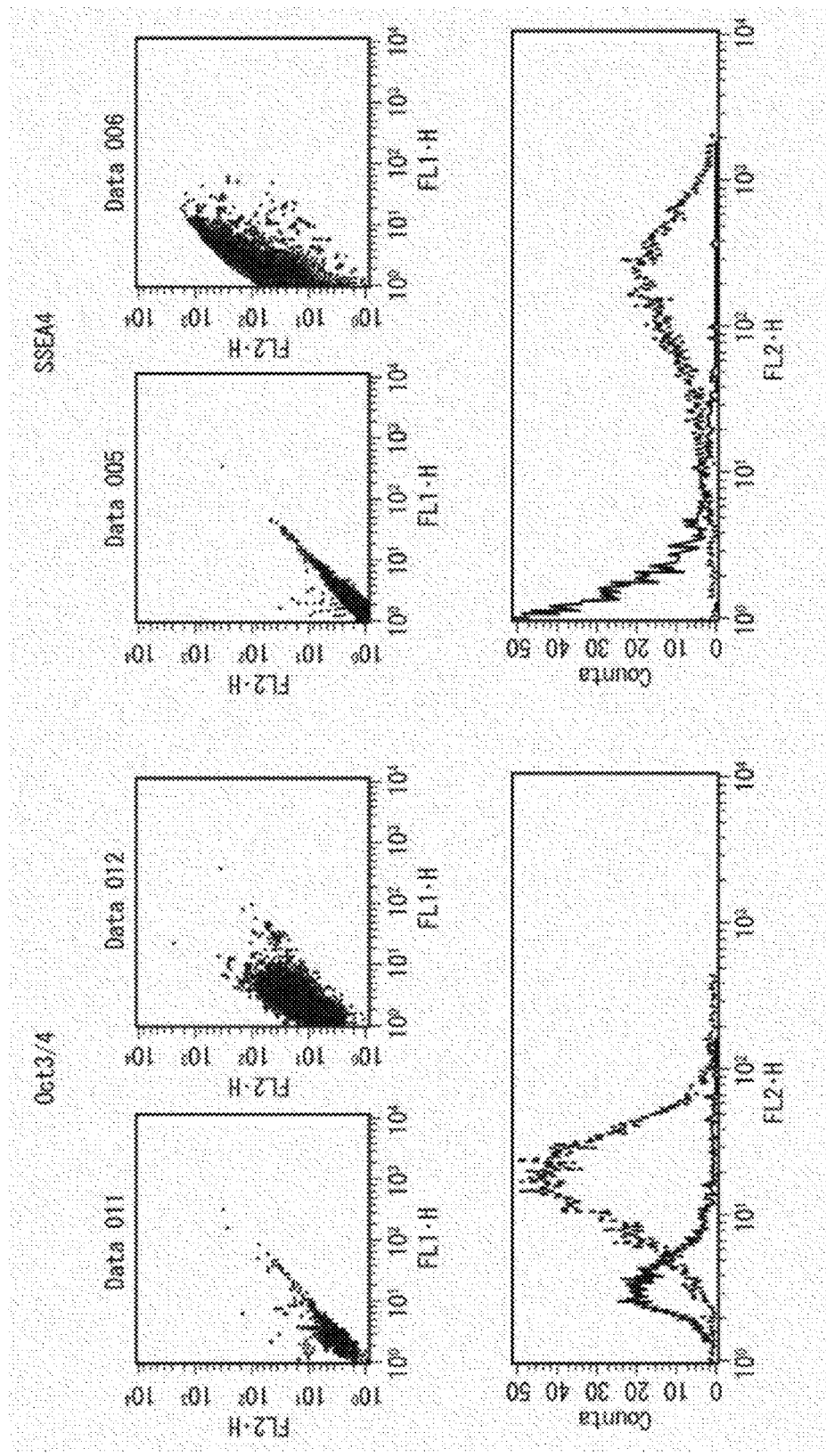
FIG. 2 includes graphs showing flow cytometoric analysis FACS (registered trademark) results showing the expressions of undifferentiation markers, SSEA4 and OCT3/4, in SeV-iPS cells.

Consequently, as shown in the results of FACS (registered trademark) shown in FIG. 2, it was confirmed that the SeV-iPS cells prepared in Example 1 highly express the undifferentiation markers, SSEA4 and OCT4.

The graphs of the upper stage show the results of analysis of SSEA4 and OCT4 expressions, where the left of each set indicates the results of staining with a control antibody and the right of each set indicates the results of staining with a target antibody (anti-SSEA4 antibody or anti-OCT4 antibody). The data of staining with the target antibodies shifted upwards with increments in FL2 values compared to those of staining with the control antibody. Thus, expressions of the target proteins were detected in the majority of the cells. The graphs of the lower stage illustrate the results shown in graphs of the upper stage as histograms. It is obvious that the distribution curves obtained with the target antibodies shifted rightwards with increments in FL2 values compared to those with the control antibody.

Furthermore, expressions of undifferentiation markers of human pluripotent stem cells, SSEA4, OCT3/4, and Nanog, were also confirmed by immunostaining.

Specifically, SeV-iPS cells prepared in Example 1 were subjected to fixation with acetone/methanol (1:3) and cell membrane permeabilization with 0.1% Triton-X-100/PBS, followed by a primary antibody reaction using an anti-human SSEA4 antibody (ES Cell Marker Sample Kit) (Millipore Co.), anti-human OCT3/4 antibody (ES Cell Marker Sample Kit) (Millipore Co.), or anti-human Nanog antibody (ReproCELL Inc.) diluted to 1/100. The reactions with the anti-human SSEA4 antibody and the anti-human OCT3/4 antibody were performed in accordance with the protocols attached to the kits. Then, a secondary antibody reaction was performed using an Alexa Fluor 488-labeled anti-rabbit IgG antibody (Life Technologies, Inc.) diluted to 1/2000, followed by observation with a fluorescence microscope.

Figure 3:
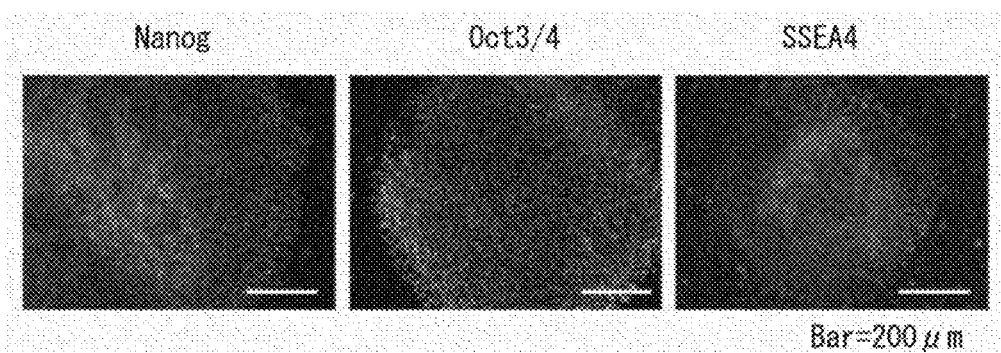
FIG. 3 includes photographs of immunostaining showing the expressions of undifferentiation markers, SSEA4, OCT3/4, and Nanog, in SeV-iPS cells.

As shown in the results of immunostaining shown in FIG. 3, it was confirmed that the SeV-iPS cells prepared in Example 1 highly express the undifferentiation markers, SSEA4, OCT4, and Nanog.

Example 3

Removal of SeV Vector-Derived Foreign Gene

SeV vector-derived foreign genes were removed from SeV-iPS cells prepared in Example 1, followed by cloning to obtain a cell line.

As a reference of removal of SeV vector-derived foreign genes, immunostaining with an anti-SeV antibody (DNAVEC Corporation) was performed. SeV-iPS cells were fixed with 10% Mildform (WAKO Pure Chemical Industries, Ltd.) and were stained using an anti-SeV antibody as a primary antibody and an Alexa Fluor 488-labeled anti-rabbit IgG antibody (Life Technologies, Inc.) as a secondary antibody, followed by observation with a fluorescence microscope.

Furthermore, transgenes and SeV genomes were detected by RT-PCR. The RT was performed using Superscript III First-Strand Synthesis System for RT-PCR (Life Technologies, Inc.). The PCR was performed using GeneAmpR PCR System 9700 (Life Technologies, Inc.) with denaturation (at 95° C. for 5 min), amplification (30 to 35 cycles of at 95° C. for 30 seconds, at 55° C. for 30 seconds, and at 72° C. for 30 seconds), and post-extension (at 72° C. for 7 min). The primers used were as follows:

```
OCT3/4
(Fw: CCCGAAAGAGAAAGCGAACCAG,

Rv: AATGTATCGAAGGTGCTCAA),

SOX2
(Fw: ACAAGAGAAAAAACATGTATGG,

Rv: ATGCGCTGGTTCACGCCCGCGCCCAGG),

KLF4
(Fw: ACAAGAGAAAAAACATGTATGG,

Rv: CGCGCTGGCAGGGCCGCTGCTCGAC), cMYC
(Fw: TAACTGACTAGCAGGCTTGTCG,

Rv: TCCACATACAGTCCTGGATGATGATG),

SeV
(Fw: GGATCACTAGGTGATATCGAGC,

Rv: ACCAGACAAGAGTTTAAGAGATATGTATC).
```

Figure 4A:
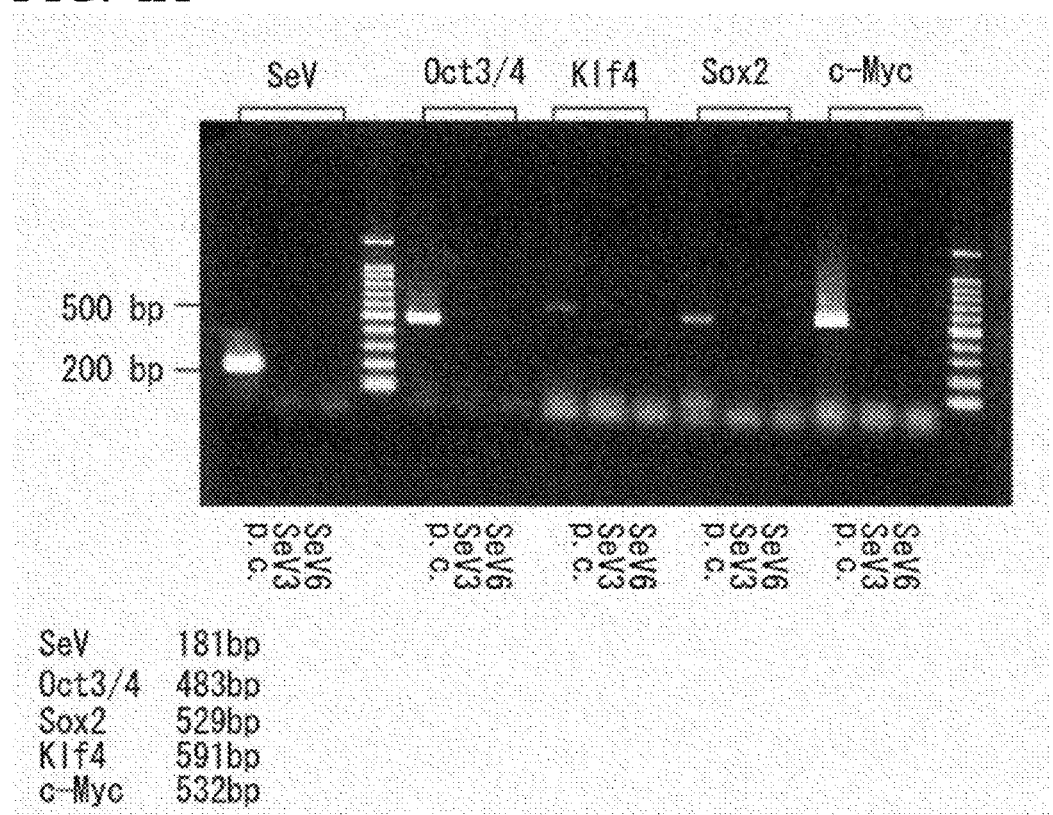
FIG. 4A is a photograph of electrophoresis showing removal of SeV vector-derived foreign genes in SeV-iPS cells.
Figure 4B:
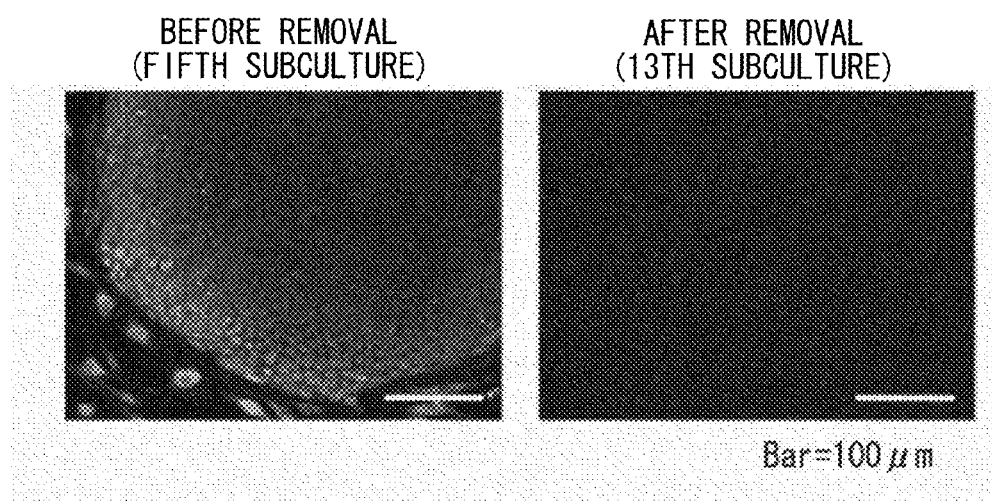
FIG. 4B includes the micrographs showing the same.

As shown in the results of electrophoresis shown in FIG. 4A and the micrographs in FIG. 4B, it was confirmed that the SeV-iPS cell line prepared in Example 1 is SeV antigen negative and therefore do not hold any SeV vector-derived foreign genes. Accordingly, the SeV-iPS cell line is suitable for clinical use and also use in a drug evaluation system or disease model system, compared to iPS cells produced with a retrovirus vector.

Example 4

Culture for Maintaining Human Embryonic Stem Cell and Human Induced Pluripotent Stem Cell The human embryonic stem cells (KhES-3) were supplied by Institute for Frontier Medical Sciences, Kyoto University. KhES-3 and SeV-iPS cell lines described in Examples 1 to 3 were subjected to maintenance culture on a MEF layer irradiated with X-ray using a medium containing a 20% Knockout Serum Replacement (KSR) (Life Technologies, Inc.), 5 ng/mL FGF 2, 1% non-essential amino acid solution, 100 μM 2-mercaptoethanol, and 2 mM L-glutamine-containing DMEM/F12 (Life Technologies, Inc.).

Example 5

Induction of Brown Adipocytes from Human Embryonic Stem Cells and Human Induced Pluripotent Stem Cells Before differentiation into brown adipocytes, a suspension of pluripotent stem cells collected by treatment with a dissociation solution for separating and removing the MEF from the KhES-3 and SeV-iPS cell lines was left to stand in a centrifuge tube for about 30 seconds to selectively precipitate only the pluripotent stem cells.

Induction of differentiation into brown adipocytes was performed by the following two steps:

(1) The precipitate, in Example 3, consisting of pluripotent stem cells was floated in 4 mL of a cell aggregate production medium (IMDM/F12 medium containing 5 mg/mL BSA, 1% by volume synthetic lipid solution, 1% by volume of ×100 ITS-A, 450 μM MTG, 2 mM L-glutamine, 5% by volume of PFHII, 50 μg/mL of ascorbic acid, 20 ng/mL of BMP4, 5 ng/mL of VEGF, 20 ng/mL of SCF, 2.5 ng/mL of Flt3L, 2.5 ng/mL of IL6, and 5 ng/mL of IGF2), and the resulting suspension was transferred in a 6-well culture plate coated with MPC, followed by culture at 37° C. in a 5% $CO_2$ incubator for 8 to 10 days while replacing a half of the medium by fresh one every 3 days. The replacement of the medium was performed by leaving the MPC-coated culture plate to stand in a state being tilted by about 30 degrees for about 1 minute to confirm the complete sedimentation of the cell aggregates, gently aspirating off a half of only the culture supernatant with a pipette, adding the same amount of a fresh medium for producing cell aggregates to the culture plate, and then uniformly dispersing the cell aggregates by lightly shaking the MPC-coated culture plate.

(2) The pluripotent stem cell-derived cell aggregates produced above were put in a centrifuge tube of about 10 mL and were left to stand for 30 seconds to 1 minute to precipitate the cell components. The supernatant was removed, and 3 mL of a brown adipocyte-inducing medium (IMDM/F12 medium containing 5 mg/mL BSA, 1% by volume of a synthetic lipid solution, 1% by volume of ×100 ITS-A, 450 μM MTG, 2 mM L-glutamine, 5% by volume of PFHII, 50 μg/mL of ascorbic acid, 10 ng/mL of BMP7, 5 ng/mL of VEGF, 20 ng/mL of SCF, 2.5 ng/mL of Flt3L, 2.5 ng/mL of IL6, and 5 ng/mL of IGF2) was added to the precipitate, followed by centrifugation at 1100 rpm for 5 minutes. The precipitate was put in a cell culture plate that was treated in advance with an aqueous 0.1% porcine gelatin solution at room temperature for 10 minutes and was incubated at 37° C. in a 5% $CO_2$ incubator for 1 week while replacing the medium by fresh one every 3 days.

Figure 5A:
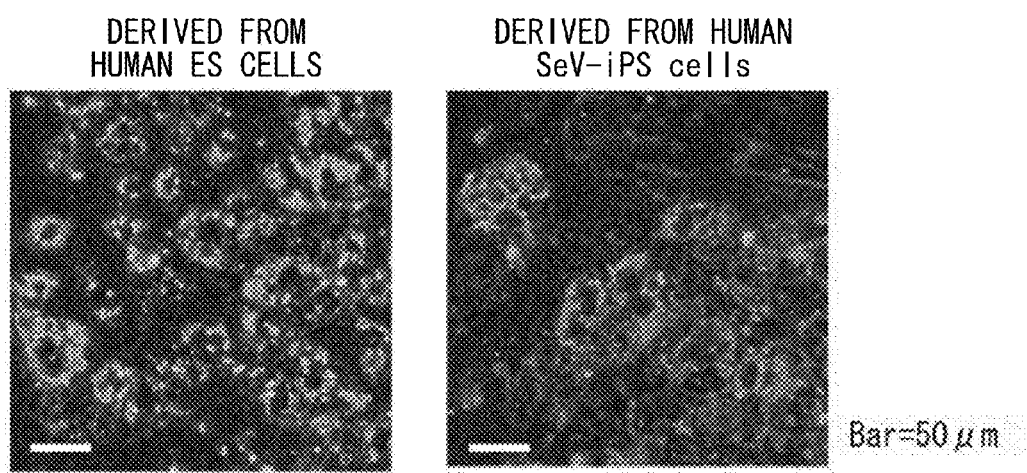
FIG. 5A includes phase contrast micrographs of brown adipocytes derived from human ES cells and human iPS cells (SeV-iPS).
Figure 5B:
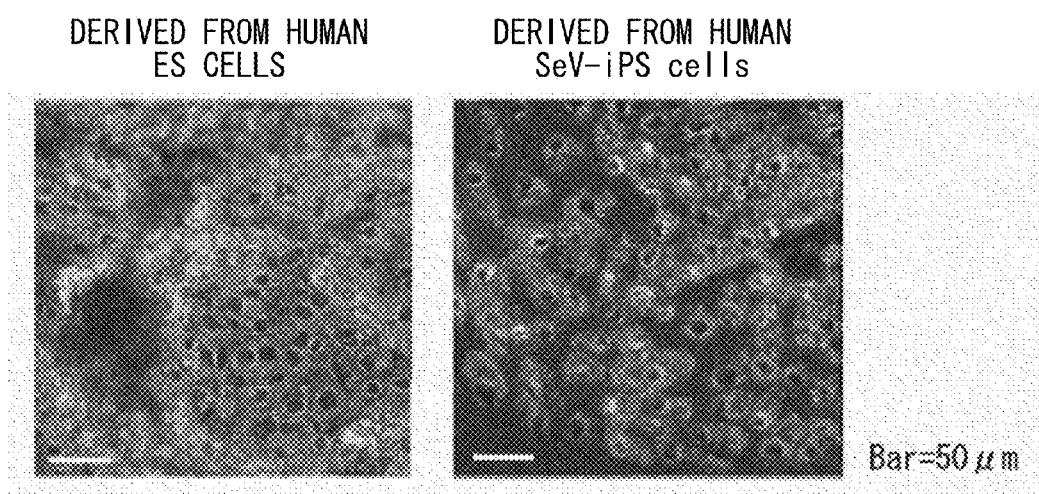
FIG. 5B includes the oil red O staining images of the same.

As a result, as shown in the phase contrast micrographs of FIG. 5A, cells having multilocular lipid droplets (a large number of yellowish and shiny spherical substance) in the cytoplasm were obtained. As shown in FIG. 5B, oil red O staining (a test of staining triglyceride into red) confirmed that the spherical substance is lipid droplets.

Figure 7A:
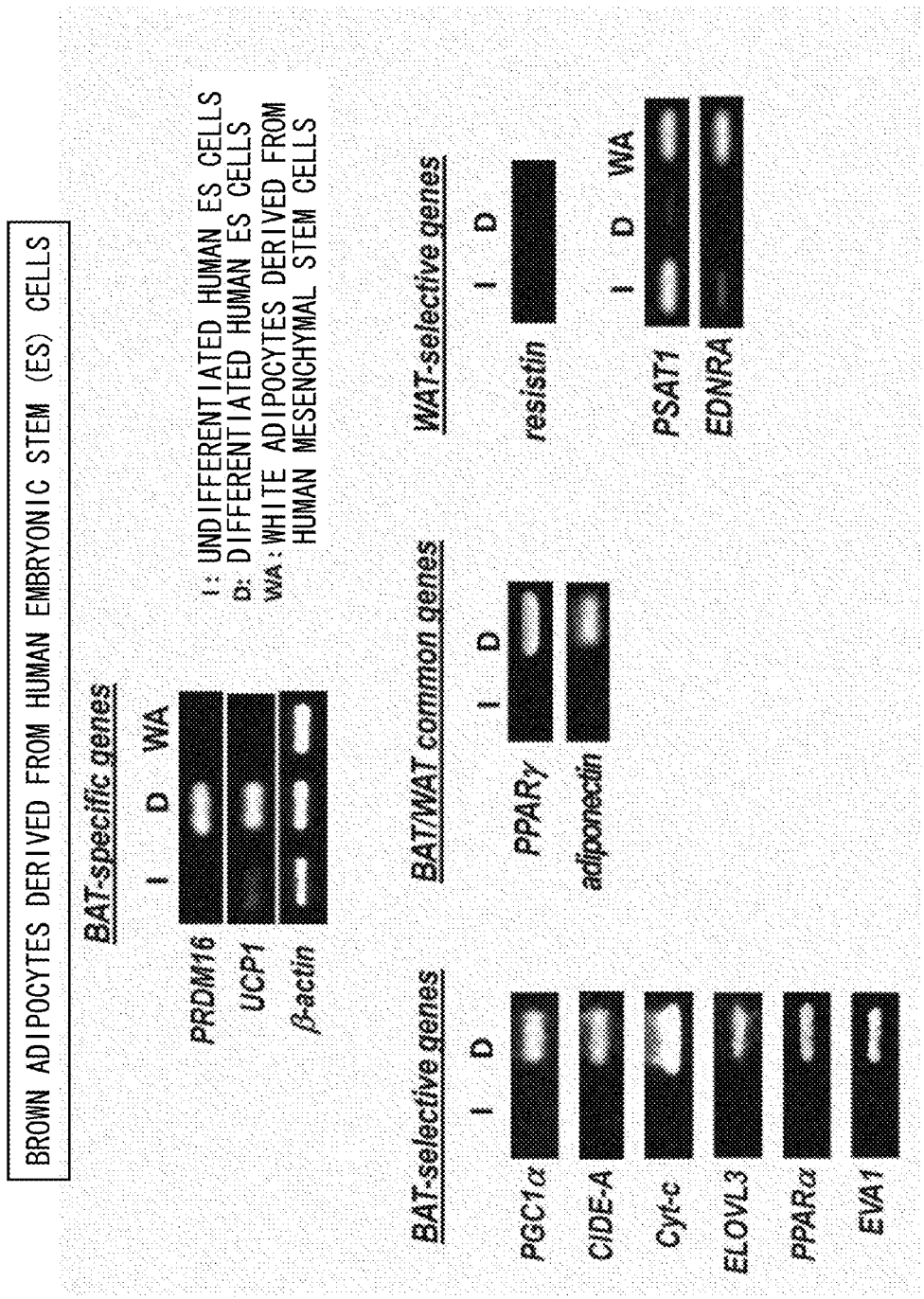
FIG. 7A includes photographs of electrophoresis of RT-PCR products from brown adipocytes differentiated from human ES cells.
Figure 7B:
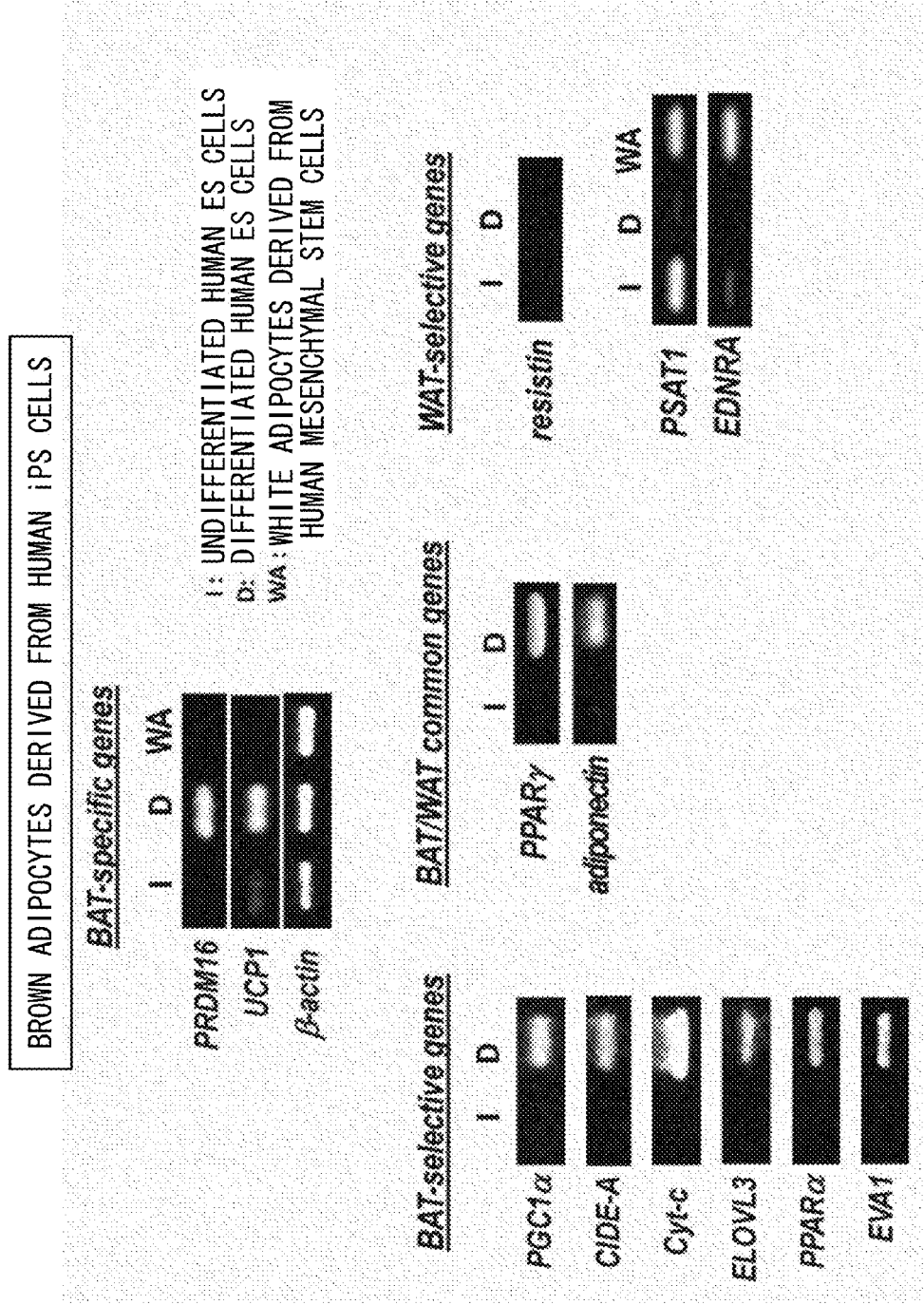
FIG. 7B includes photographs of electrophoresis of RT-PCR products from brown adipocytes differentiated from human iPS cells (SeV-iPS).

As shown by the electrophoresis in FIG. 7, RT-PCR using the primers shown in FIG. 6 confirmed that the expressions of a gene cluster (UCP1, PRDM16, PGC1α, Cyt-c, CIDE-A, ELOVL3, PPARα, EVA1, and NTRK3) characteristic to brown adipocytes were induced. It was also confirmed that the expressions of PPARγ and adiponectin, which are markers common to brown adipocytes and white adipocytes, were also inducted, whereas the expressions of resistin, phosphoserine transaminase 1 (PSAT1), and endothelin receptor alpha (EDNRA), which are makers specific to white adipocytes, were not induced.

Resistin is a gene that not only induces insulin resistance but is also involved in canceration and arteriosclerosis. The result that the expression of resistin is not induced in brown adipocytes derived from human pluripotent stem cells is significantly important not only for drug discovery research using the human pluripotent stem cell-derived brown adipocytes and also for safety in cell therapy using the human pluripotent stem cell-derived brown adipocytes.

Figure 8:
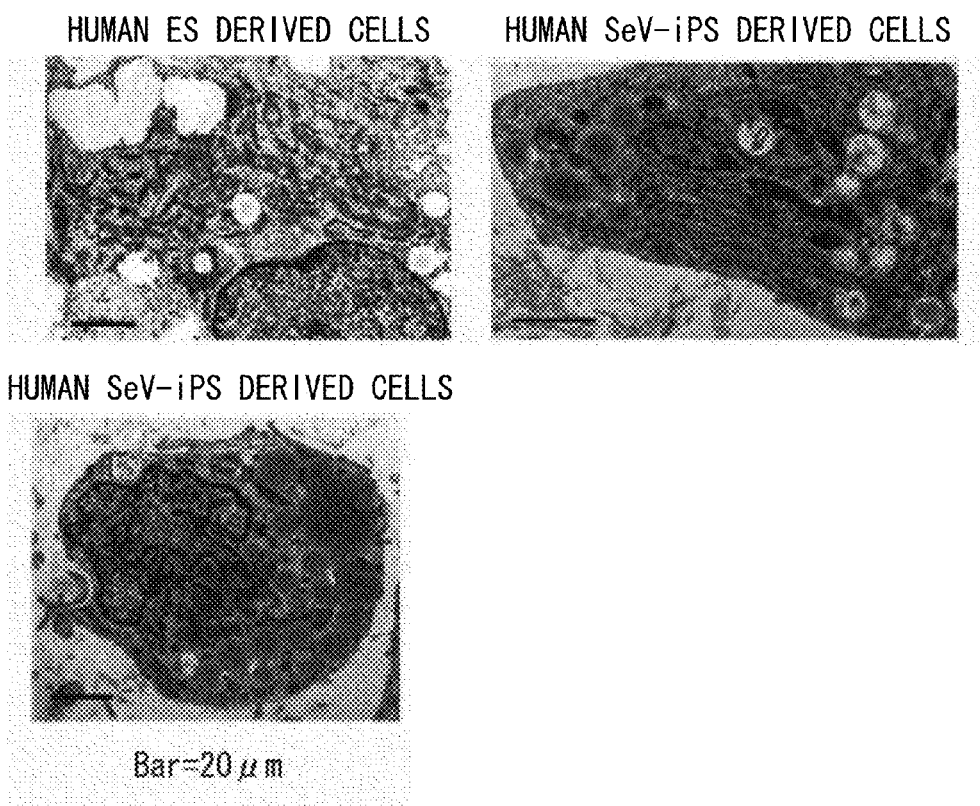
FIG. 8 includes electron micrographs of brown adipocytes differentiated from pluripotent stem cells.

As shown by the electron micrographs in FIG. 8, multilocular lipid droplets, which are fine structures characteristic to brown adipocytes, and mitochondria fused long lengthwise were confirmed. Furthermore, developed ladder-type cristae, which are characteristic to brown adipocytes, were confirmed inside the mitochondria.

Example 6

Confirmation of Necessity of a Hematopoietic Cytokine and Effectiveness of BMP7 in Induction of Brown Adipocytes from Human Embryonic Stem Cells and Human Induced Pluripotent Stem Cells In differentiation into brown adipocytes from KhES-3 and SeV-iPS cell lines in accordance with the method described in Example 5, the suspension culture in the step (A) was performed in a medium not containing hematopoietic cytokines but containing only 5 ng/mL of IGF2 and 20 ng/mL of BMP4 as cytokines. As a result, a large amount of cell death was induced, and no cell aggregate was formed at all. That is, a hematopoietic cytokine cocktail is indispensable in the step (A) for producing cell aggregates as the first half of the differentiation process of human pluripotent stem cells into brown adipocytes.

Furthermore, in order to evaluate necessity of hematopoietic cytokines and BMP7 in the latter half of the differentiation process of human pluripotent stem cells into brown adipocytes in the suspension culture in the step (A), cell aggregates were produced using the medium containing 20 ng/mL of BMP4, 5 ng/mL of VEGF, 20 ng/mL of SCF, 2.5 ng/mL of Flt3L, 2.5 ng/mL of IL6, and 5 ng/mL of IGF2 described in Example 5, and the subsequent adhesion culture in the step (B) was performed using a medium containing a hematopoietic cytokine cocktail and BMP7 or a medium not containing them, followed by investigation of the induction states of expressions of UCP1 and PRDM16 genes and the cellular morphology thereof.

Figure 9A:
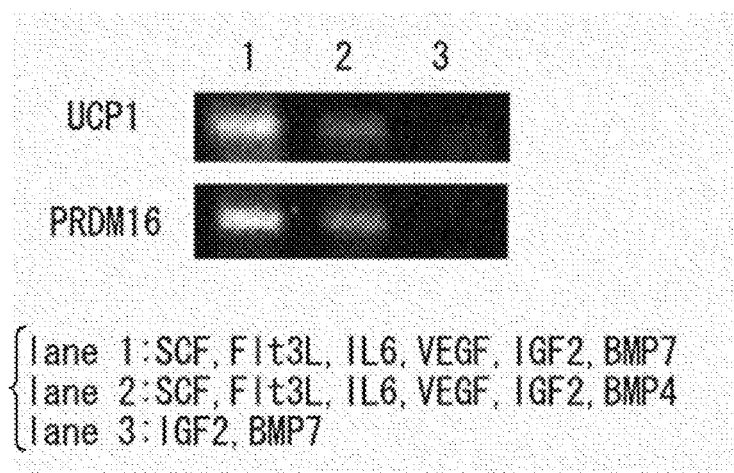
FIG. 9A includes photographs of electrophoresis of RT-PCR products showing the necessity of a hematopoietic cytokine and effectiveness of BMP7 in differentiation from human iPS cells (SeV-iPS) to brown adipocytes.

As a result, in the experiments using human induced pluripotent stem cells, both expressions of UCP1 and RPDM16 genes were not induced when a medium not containing the hematopoietic cytokine cocktail was used in the adhesion culture in the step (B) (FIG. 9A, lane 3). When a medium not containing BMP7 but containing BMP4 (FIG. 9A, lane 2) was used, the induction of the expressions was low in both UCP1 and RPDM16 genes, compared to the case using a medium containing BMP7 (FIG. 9A, lane 1).

Figure 9B:
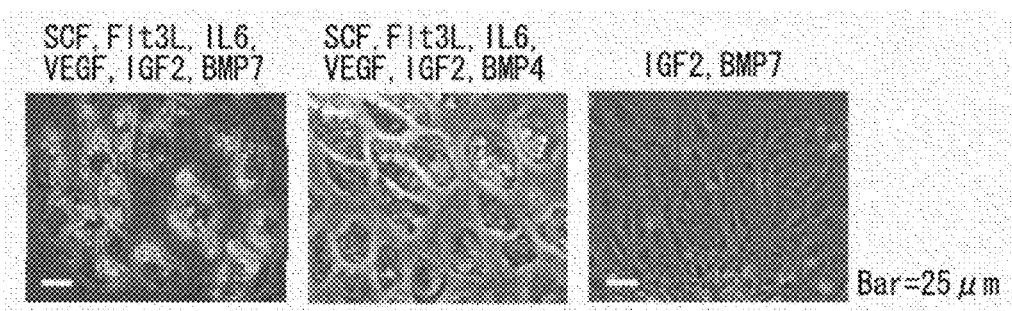
FIG. 9B includes the phase contrast micrographs of the same.

In addition, as shown in FIG. 9B, in the phase contrast microscopic observation of the cells, when a medium not containing any hematopoietic cytokine cocktail was used in the adhesion culture of the step (B), no cells which contain lipid droplets in the cytoplasm were detected. Cells containing lipid droplets in the cytoplasm were detected in the culture using a medium not containing BMP7 but containing BMP4, but the number of the cells containing lipid droplets was smaller than that when a medium containing BMP7 was used.

Figure 9C:
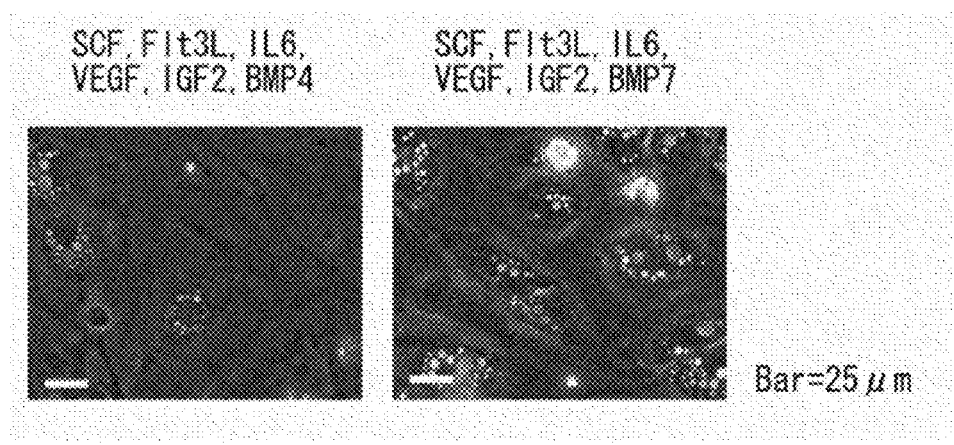
FIG. 9C includes phase contrast micrographs showing the effectiveness of BMP7 in differentiation from human ES cells to brown adipocytes.

This activity of BMP7 was similarly confirmed in the experiment using human embryonic stem cells (FIG. 9C).

Furthermore, in order to confirm the necessity of each of the hematopoietic cytokines (VEGF, SCF, Flt3L, and IL6), differentiation was induced using cytokine cocktails, each of which does not contain any one of the cytokines.

Figure 9D:
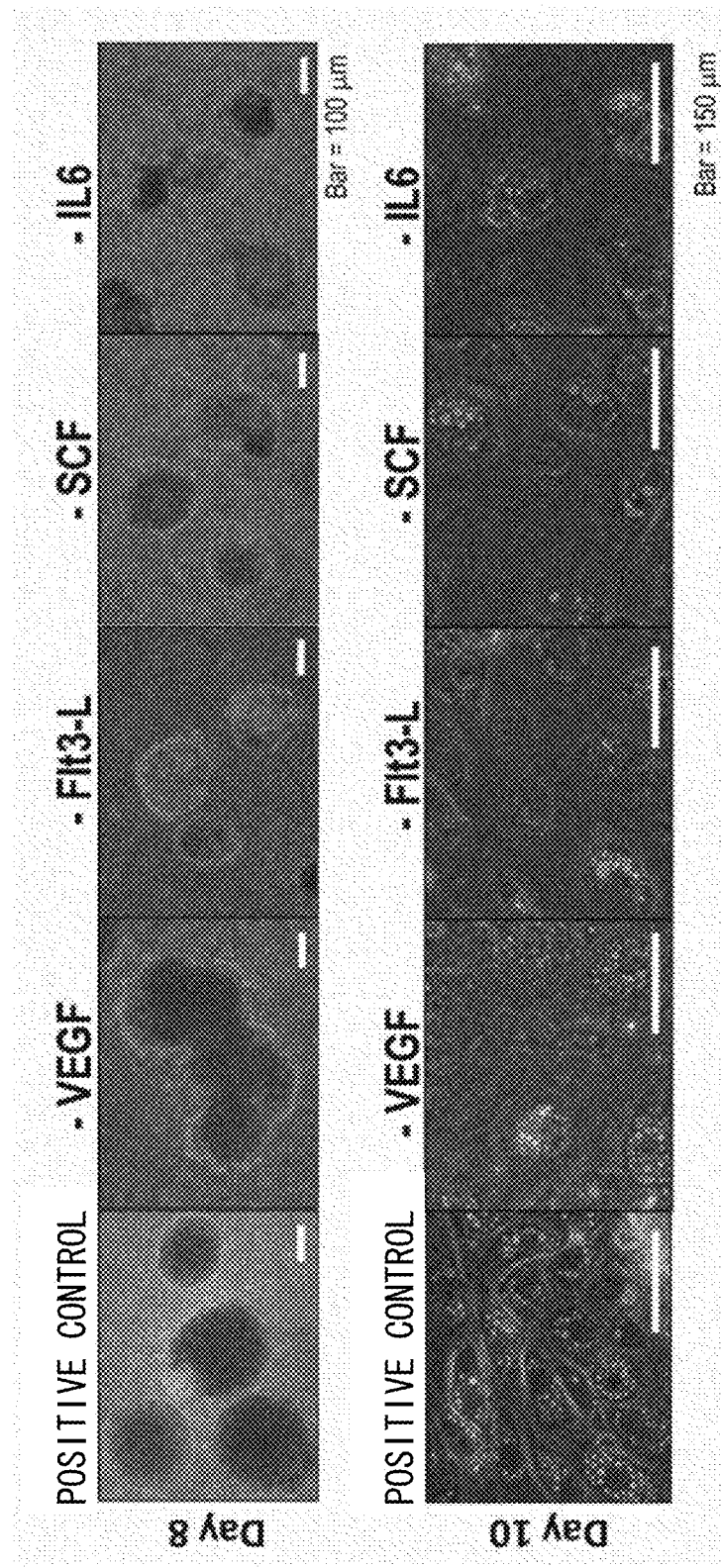
FIG. 9D includes phase contrast micrographs of brown adipocytes differentiated from pluripotent stem cells under conditions not containing any hematopoietic cytokine.

In the step (A) of producing cell aggregates as the first half of the differentiation process of human pluripotent stem cells to brown adipocytes, as shown in the upper side (Day 8) of FIG. 9D, it was confirmed that the removal of one cytokine from the medium increased the amorphous morphology of the cell aggregates and reduced the cell viability such as floating of dead cells that were not uptaken into cell aggregates in the medium, compared to the case of using a medium (positive control) containing all of the cytokines. In the step (B) of adhesion culture of cell aggregates as the latter half of the differentiation process of human pluripotent stem cells to brown adipocytes, as shown in the lower side (Day 10) of FIG. 9D, the removal of one cytokine from the medium reduced the ratio of cells having multilocular lipid droplets compared to the case of using a medium (positive control) containing all of the cytokines.

Figure 9E:
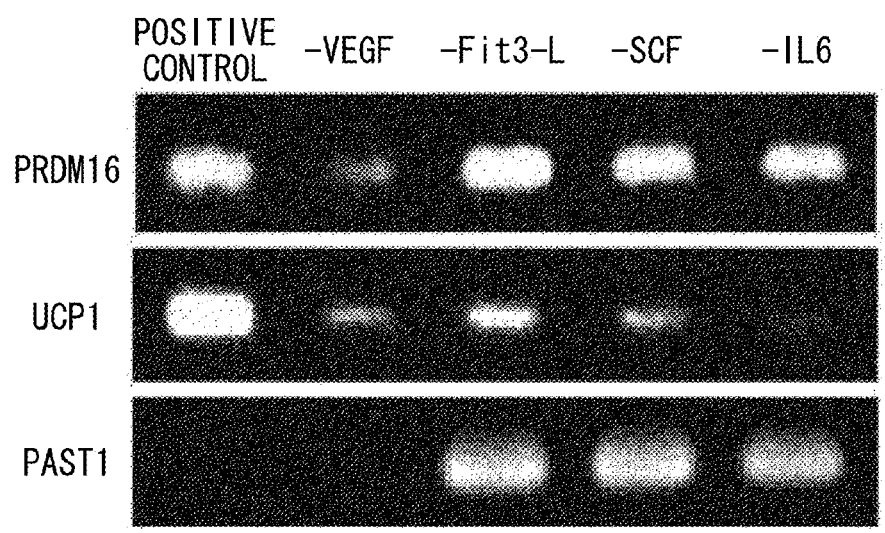
FIG. 9E includes photographs of electrophoresis of RT-PCR products in differentiation from pluripotent stem cells to brown adipocytes under conditions not containing any hematopoietic cytokine.

In order to quantitatively evaluate the above, the total RNA was extracted from the product produced under each condition for differentiation induction, and RT PCR was carried out. The results revealed, as shown in FIG. 9E, that the removal of VEGF significantly reduces the induction of PRDM16 and UCP1 compared to the medium (positive control) containing all cytokines. It was also revealed that though the expression of PRDM 16 is induced when SCF, Flt3-L, or L6 is removed, the induction of the expression of UCP1 is significantly reduced. Furthermore, it was revealed that the expression of PSAT1, which is a marker of white adipocytes, is induced when SCF, Flt3-L, or L6 is removed. Thus, it was revealed that the removal of any of the cytokines reduces not only the efficiency of differentiating into brown adipocytes but also the quality of the resulting brown adipocytes.

Example 7

Confirmation of Increase in "Thermogenesis" by Adrenergic β Receptor Agonist in Brown Adipocytes Produced from Human Embryonic Stem Cells and Human Induced Pluripotent Stem Cells Brown adipocytes were produced from KhES-3 cell line and SeV-iPS cell line in accordance with the method described in Example 5 and were reacted with 100 μM of an adrenaline receptor agonist, isoproterenol, for 4 hours. In order to evaluate the activation of the brown adipocytes by the addition of the adrenaline receptor agonist, the expressions of the PRDM16 and UCP1 genes were investigated by RT-PCR.

Figure 10:
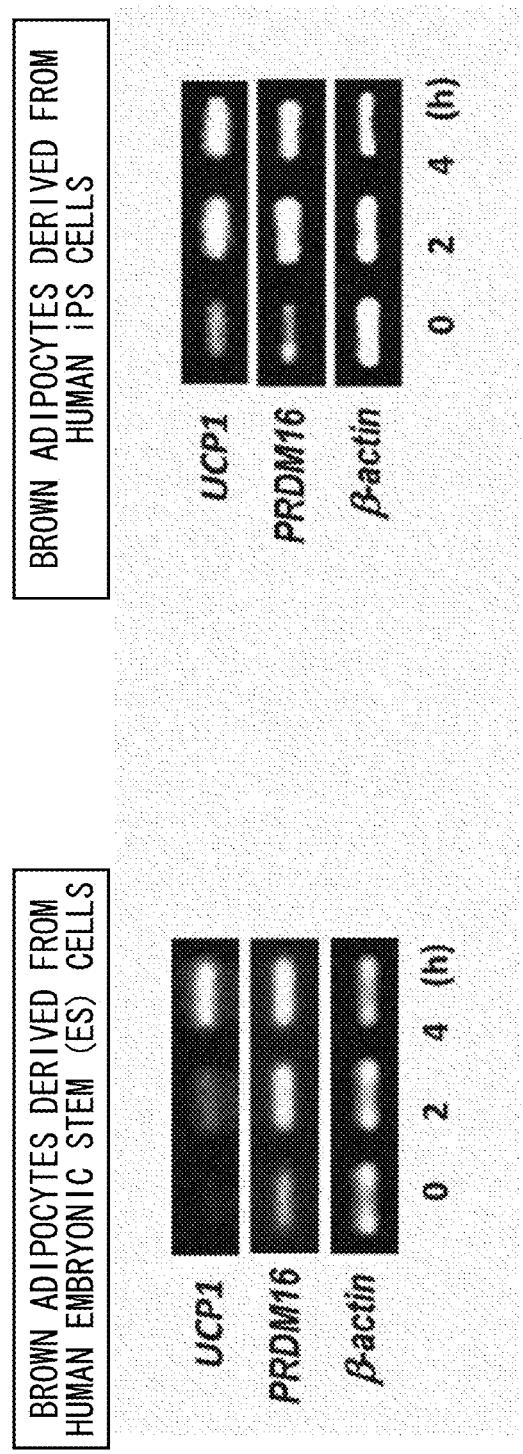
FIG. 10 includes photographs of electrophoresis of RT-PCR products showing increases in the expression of UCP1 and PRDM16 genes when an adrenergic β receptor agonist was added to brown adipocytes differentiated from pluripotent stem cells.

As a result, as shown in FIG. 10, an increase in the expression of the UCP1 gene, which is indispensable to thermogenesis, was observed, together with an increase in the expression of the PRDM16 gene, depending on the addition of isoproterenol.

Furthermore, in order to confirm the in vivo thermogenesis function of brown adipocytes produced from human pluripotent stem cells, the following experiment was conducted. Brown adipocytes ($1\times10^6$ cells/100 μL physiological saline (saline)) produced from KhES-3 cell line or SeV-iPS cells were subcutaneously transplanted in each 6-week old mouse (ICR strain) (on the back) depilated in advance 3 days before. On the following day of the transplantation, isoproterenol (30 μmol/kg) was administered to the mice. After 4 hours, a thermographic photograph of the mice under anesthesia was taken with Thermo GEAR G120 (manufactured by NEC Avio Infrared Technologies Co., Ltd). As a negative control, saline (100 μL) and undifferentiated KhES-3 cells ($1\times10^6$ cells/100 μL saline) or saline (100 μL) and undifferentiated SeV-iPS cells ($1\times10^6$ cells/100 μL saline) were transplanted.

Figure 11A:
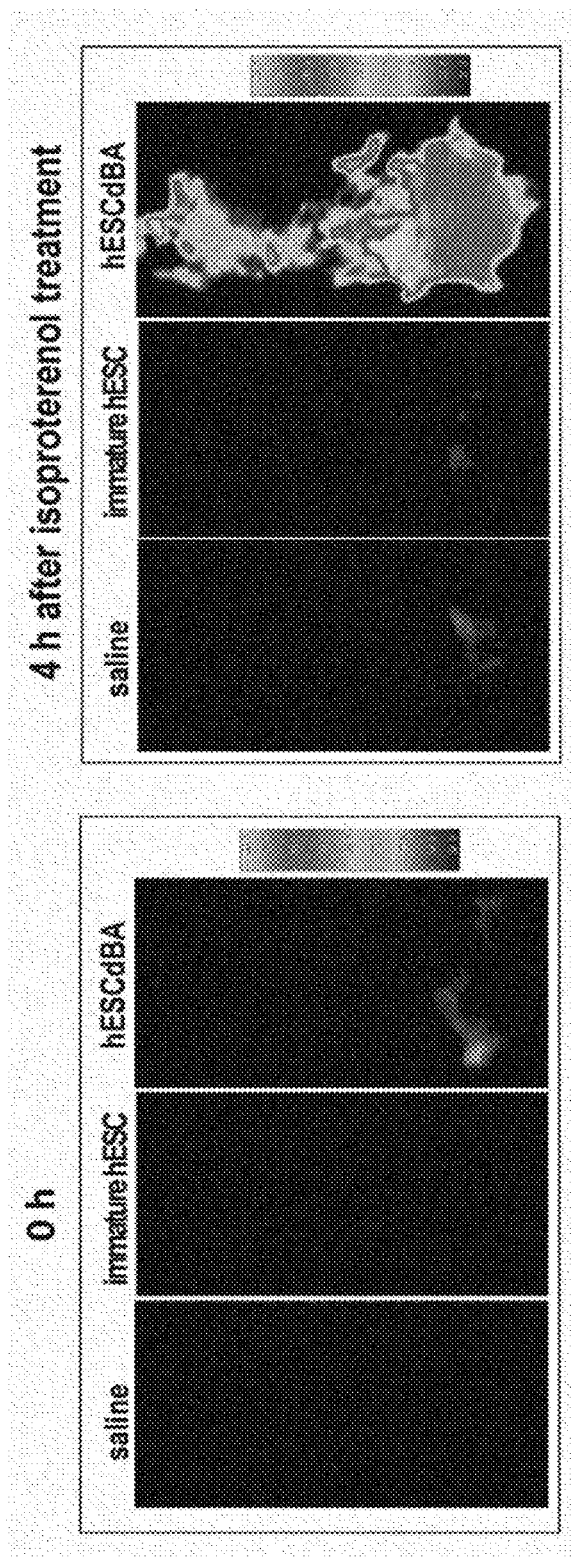
FIG. 11A includes photographs showing changes in the body surface temperature when brown adipocytes differentiated from human ES cells were subcutaneously transplanted on the back of mice and an adrenergic β receptor agonist was added thereto.
Figure 11B:
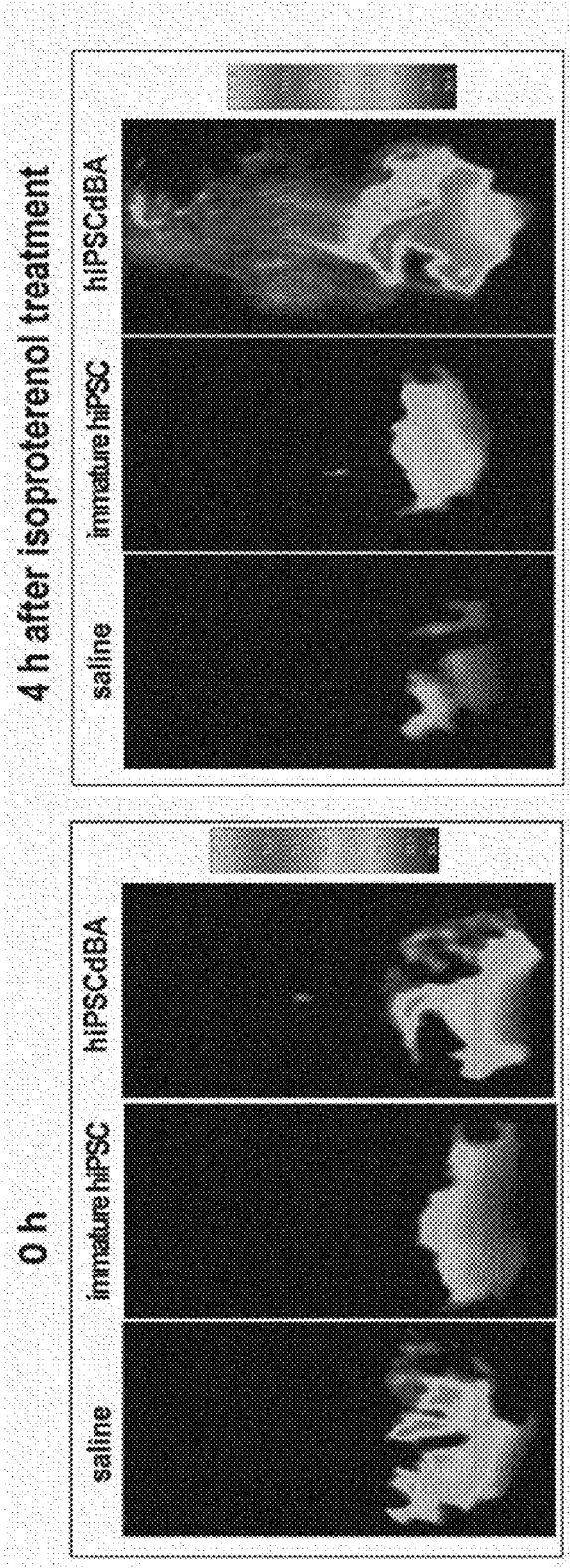
FIG. 11B includes photographs showing changes in the body surface temperature when brown adipocytes differentiated from human iPS cells (SeV-iPS) were subcutaneously transplanted on the back of mice and an adrenergic β receptor agonist was added thereto.

As a result, as shown in FIG. 11 (the right in FIG. 11A and the right in FIG. 11B), an increase in the skin temperature at the transplantation site was observed only in the mice transplanted with the brown adipocytes derived from human pluripotent stem cells.

Example 8

Confirmation of Enhancement in Mitochondrial Respiration Ability by Adrenaline β3 Receptor Agonist in Brown Adipocytes Produced from Human Embryonic Stem Cells and Human Induced Pluripotent Stem Cells Brown adipocytes were differentiated from KhES-3 and SeV-iPS cell lines in accordance with the method described in Example 5. Here, the adhesion culture in the step (B) for differentiation induction was carried out using a 96-well plate for exclusive use in XF96 Extracellular Flux Analyzer (Seahorse Bioscience Inc., Billerica, Mass.) after coating with 0.1% gelatin. The cell aggregates were seeded at an amount of 30 cell aggregates per well. The cell aggregates seeded in the 96-well plate were incubated in a 5% $CO_2$ incubator at 37° C. for 2 days. Subsequently, isoproterenol (100 μM) or CL316,243 (100 nM) was added to a half of the wells, and incubation was further carried out in a 5% $CO_2$ incubator at 37° C. for 4 hours, followed by measurement of oxygen consumption (OCR) per minute with XF96 Extracellular Flux Analyzer (Seahorse Bioscience Inc., Billerica, Mass.).

Figure 12A:
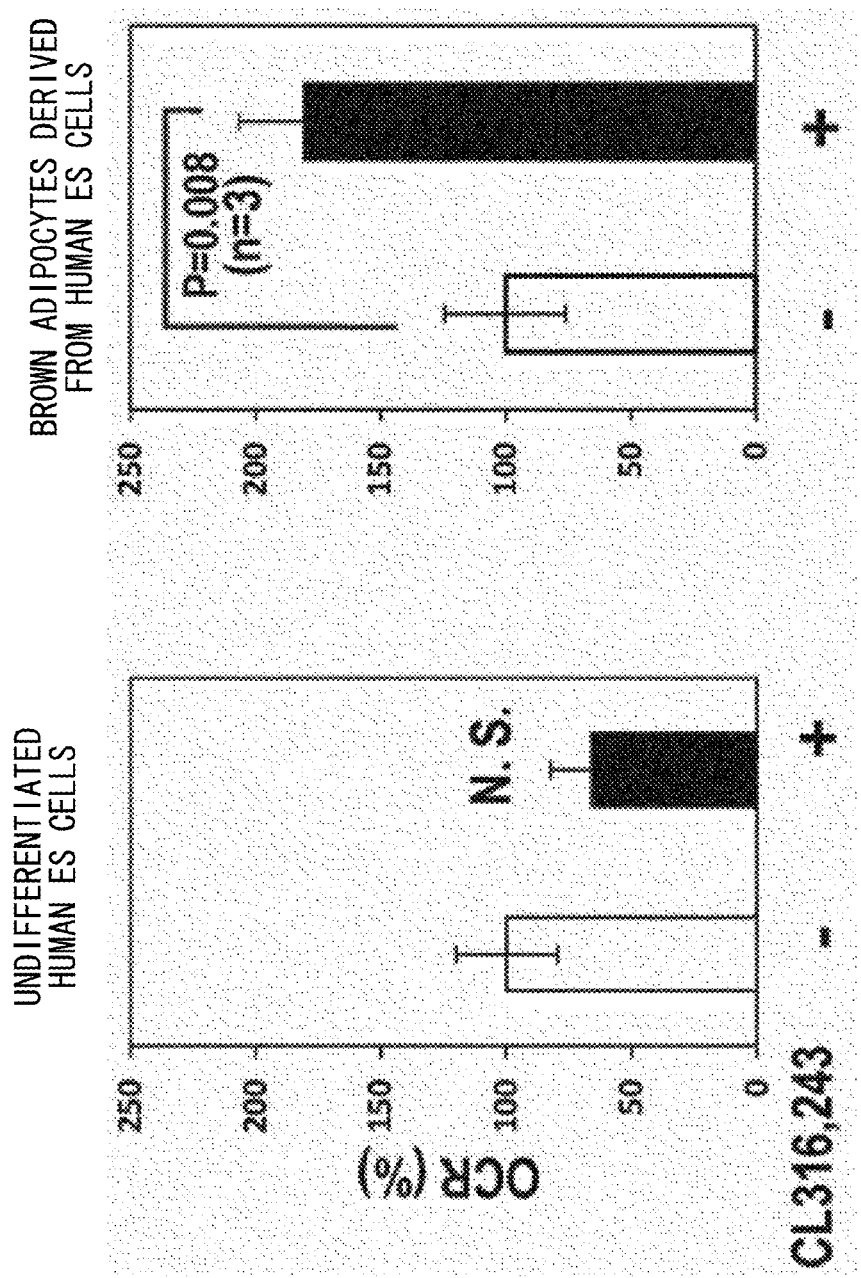
FIG. 12A includes graphs showing the evaluation results of mitochondrial respiration ability of brown adipocytes differentiated from human ES cells.
Figure 12B:
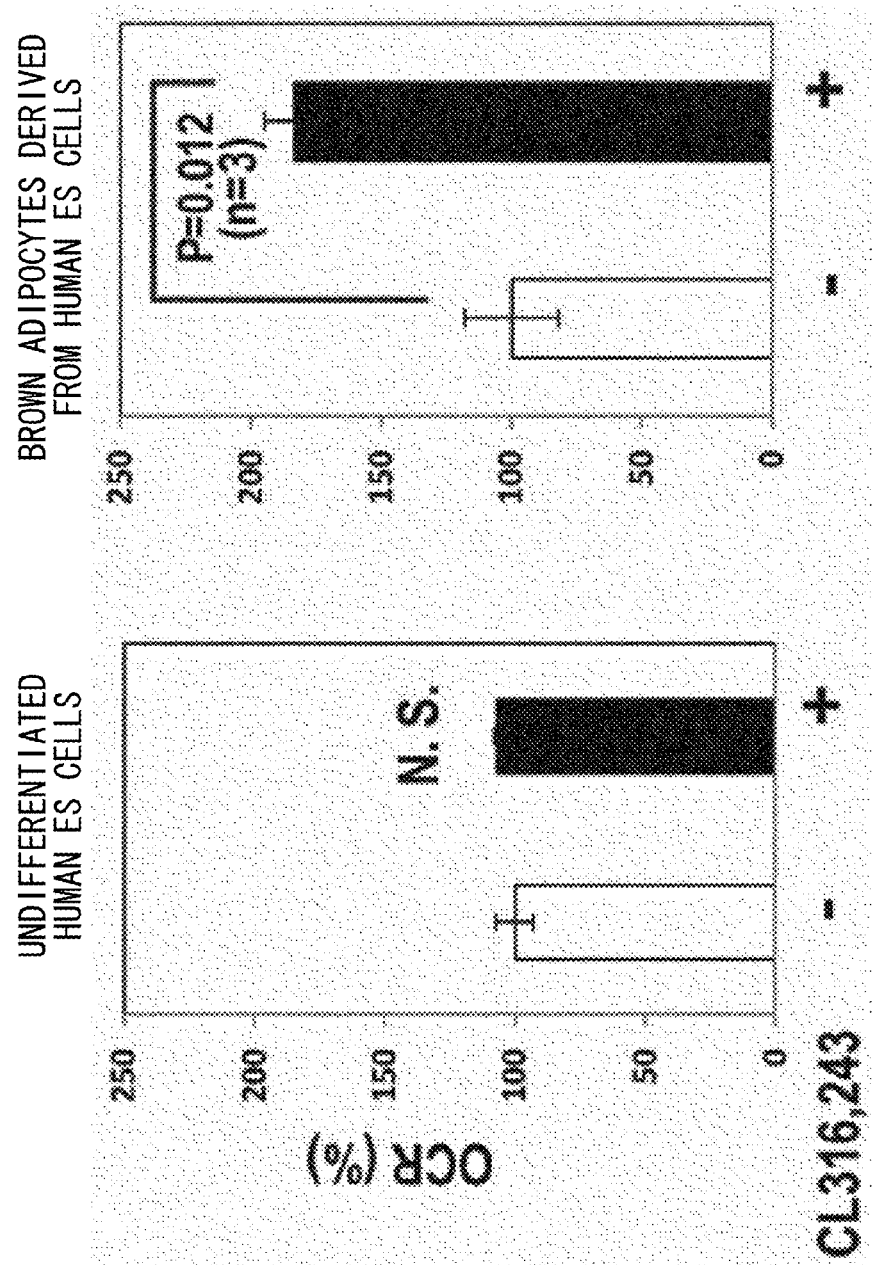
FIG. 12B includes graphs showing the evaluation results of mitochondrial respiration ability of brown adipocytes differentiated from human iPS cells (SeV-iPS).
Figure 12C:
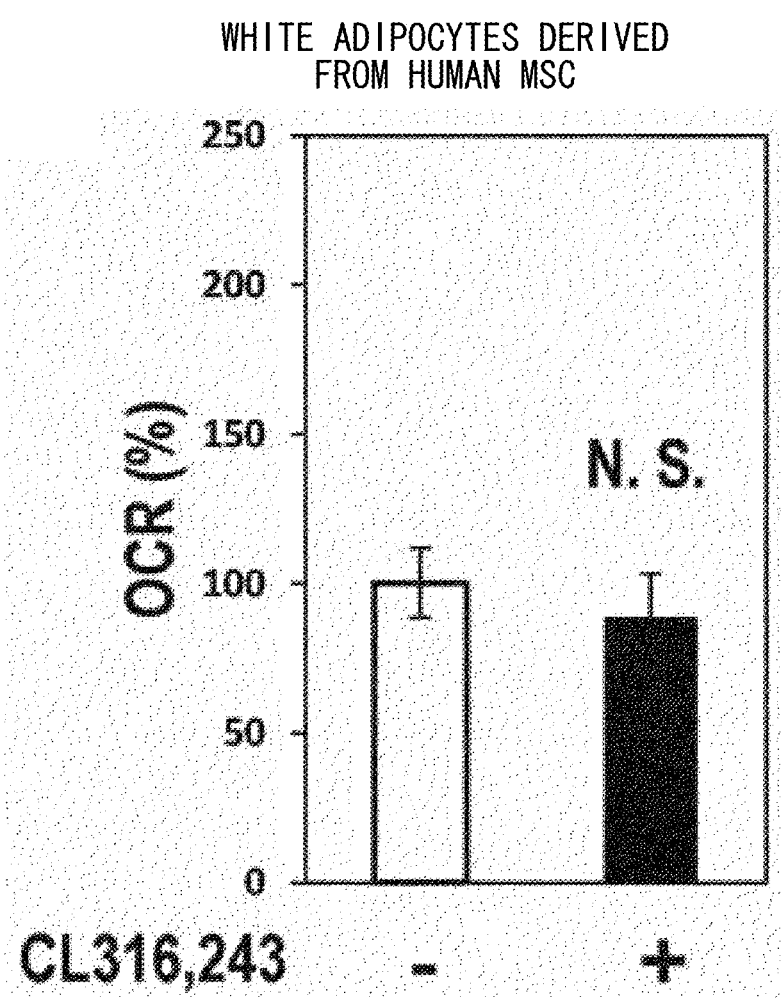
FIG. 12C is a graph showing the evaluation results of mitochondrial respiration ability of white adipocytes derived from human MSCs.

The results demonstrated, as shown in FIG. 12, that a significant increase in OCR value depending on administration of CL316,243 was observed in brown adipocytes derived from human ES cells (the right in FIG. 12A) and brown adipocytes derived from human iPS cells (the right in FIG. 12B), whereas no change in OCR value by the administration of CL316,243 was observed in undifferentiated human ES cells (the left in FIG. 12A) and undifferentiated human iPS cells (the left in FIG. 12B). Similar results were also observed in stimulation with isoproterenol. In white adipocytes produced from human mesenchymal stem cells (MSCs), no change in OCR value by CL316,243 administration was recognized (FIG. 12C). Similar results were also obtained in isoproterenol administration.

Example 9

Confirmation of Effect of Removing Triglyceride (TG) from Blood by Brown Adipocytes Produced from Human Embryonic Stem Cells and Human Induced Pluripotent Stem Cells First, the effect of removing fasting blood TG was investigated. Specifically, brown adipocytes were produced from human ES cells (hES-3 cell line) by the method described in Example 5. The resulting human ES cell-derived brown adipocytes ($1 \times 10^6$ cells) were subcutaneously transplanted into each 6-week old mouse (ICR strain) (on the back). After fasting for 16 hours, isoproterenol (30 μmol/kg) was administered to the mice. After 2 hours from the administration, a small amount of blood (about 5 μL) was sampled from the lateral tarsal vein and was subjected to measurement of TG level (mM/L) with Accutrend Plus (registered trademark) (F. Hoffmann-La Roche, Ltd., Basel, Switzerland). As a negative control, undifferentiated human ES cells (KhES-3 cell line) were used. As a positive control, white adipocytes (WAs) produced from human mesenchymal stem cells (MSCs, Lonza Group Ltd., Basel, Switzerland) using an adipocyte differentiation induction kit (hMSC Differentiation Bullet Kit™, Adipogenic, Lonza Group Ltd) were used.

Figure 13A:
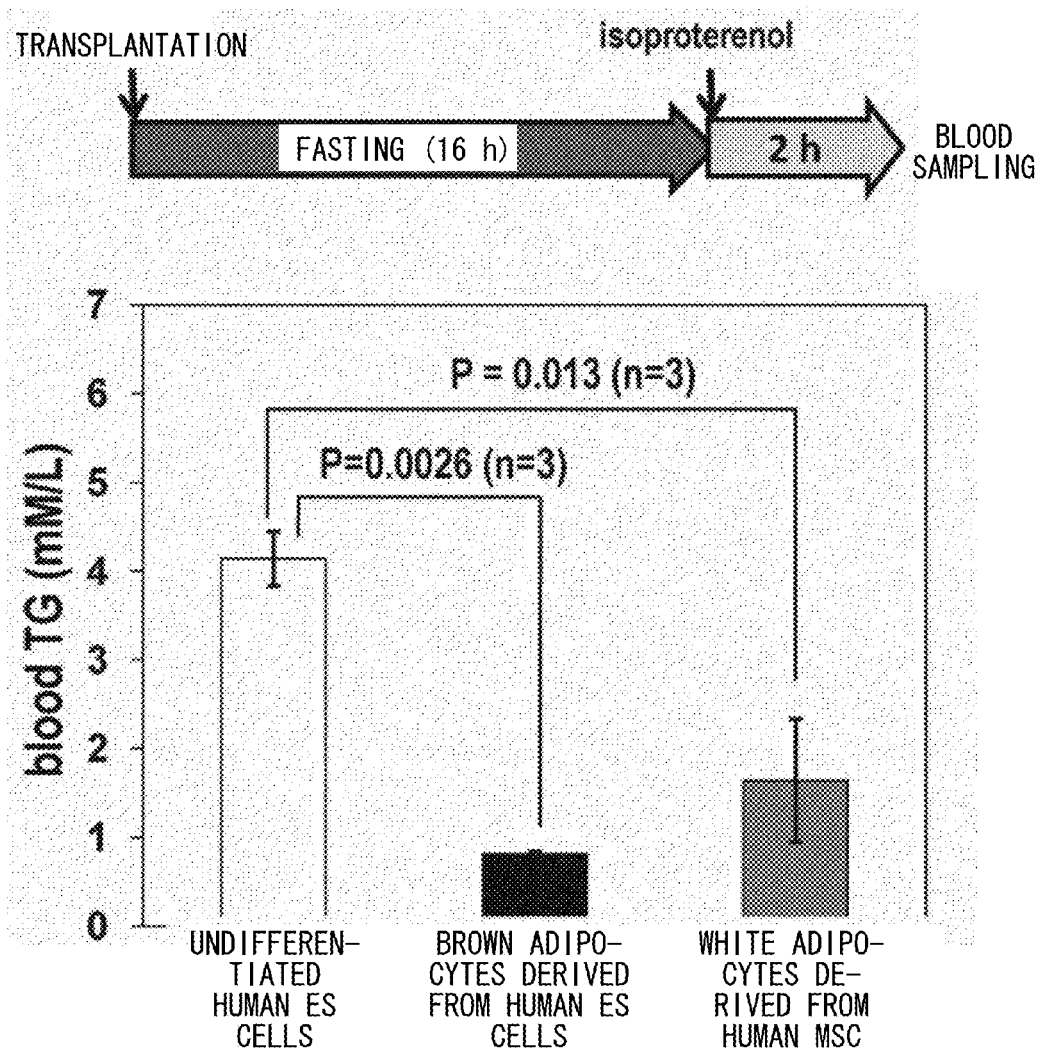
FIG. 13A is a graph showing changes in blood triglyceride level when brown adipocytes differentiated from human ES cells were subcutaneously transplanted on the back of mice and an adrenergic α receptor agonist was added thereto.

As a result, as shown in FIG. 13A, it was confirmed that the transplantation of human ES cell-derived brown adipocytes significantly reduces the fasting blood TG level. In addition, the effect of reducing the TG level by brown adipocytes derived from human ES cells was notably higher than that by white adipocytes derived from human MSCs.

Next, the effect of removing the blood TG after loading with fat through oral administration was investigated. Specifically, brown adipocytes were produced from human iPS cells (SeV-iPS cell line) by the method described in Example 5. The resulting human iPS cell-derived brown adipocytes ($1 \times 10^6$ cells) were subcutaneously transplanted into each 6-week old mouse (ICR strain) (on the back). After fasting for 16 hours, isoproterenol (15 μmol/kg) was administered to the mouse. After 2 hours from the administration, olive oil (200 μL) was orally administered with a sonde. A small amount of blood (about 5 μL) was sampled from the lateral tarsal vein every 2 hours after the administration of isoproterenol and was subjected to measurement of TG level (mM/L) with Accutrend Plus (registered trademark) (F. Hoffmann-La Roche, Ltd.). As a negative control, a similar experiment was carried out by transplanting undifferentiated human iPS cells (SeV-iPS cell line) ($1 \times 10^6$ cells).

The results, as shown in FIG. 13B, demonstrated that transplantation of human iPS cell-derived brown adipocytes significantly inhibits the increase in blood TG level after olive oil loading.

Accordingly, it was demonstrated that human ES cell-derived brown adipocytes and human iPS cell-derived brown adipocytes have an activity of removing blood TG and that they show an effect of improving lipid metabolism in vivo.

This lipid metabolism-improving effect is believed to be based on a possibility of direct uptake of blood TG by human pluripotent stem cell-derived brown adipocytes, a possibility of activity of adipokines secreted by human pluripotent stem cell-derived brown adipocytes on other organs (such as liver, skeletal muscle, or white adipocytes) to improve the lipid metabolism, or both possibilities.

Example 10

Figure 14A:
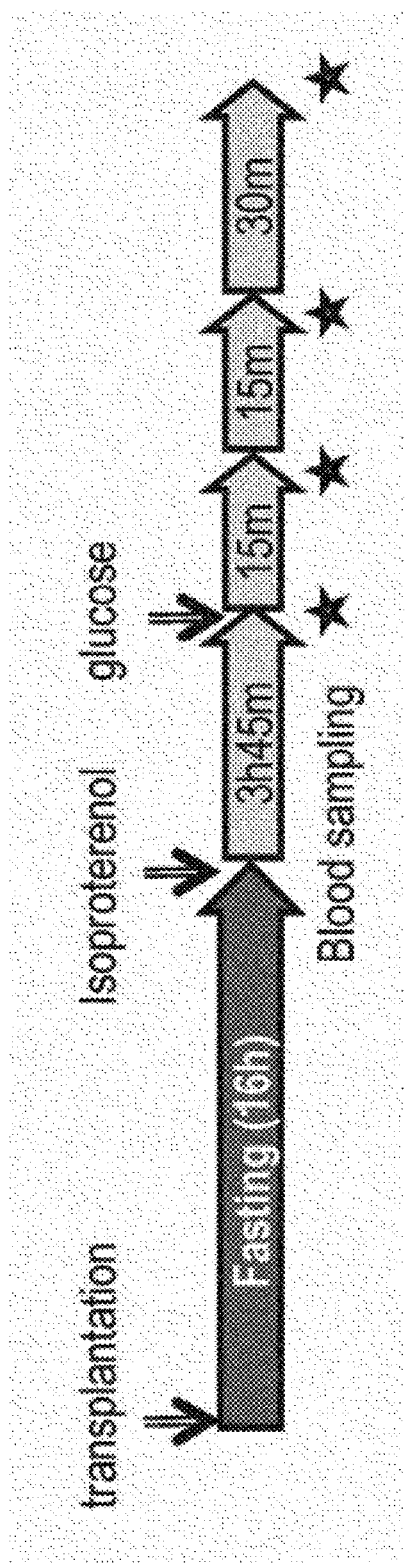
FIG. 14A is an explanatory drawing of a glucose tolerance test schedule.

Confirmation of Effect of Improving Glucose Metabolism by Brown Adipocytes Produced from Human Embryonic Stem (ES) Cells Brown adipocytes were produced from KhES-3 cell line in accordance with the method described in Example 5. The resulting human ES cell-derived brown adipocytes ($1 \times 10^6$ cells) were subcutaneously transplanted into each 6-week old mouse (ICR strain) (on the back). After fasting for 16 hours, isoproterenol (30 μmol/kg) was administered to the mice. After 3 hours and 45 minutes from the administration, glucose (2 mg/weight (g) of mouse) was orally administered with a sonde. The blood was sampled before the glucose administration and at 15 min, 30 min, and 60 min after the administration, and the blood glucose concentrations (blood glucose levels) were measured (FIG. 14A). As a control, a similar experiment was carried out using white adipocytes produced from human MSCs.

Figure 14B:
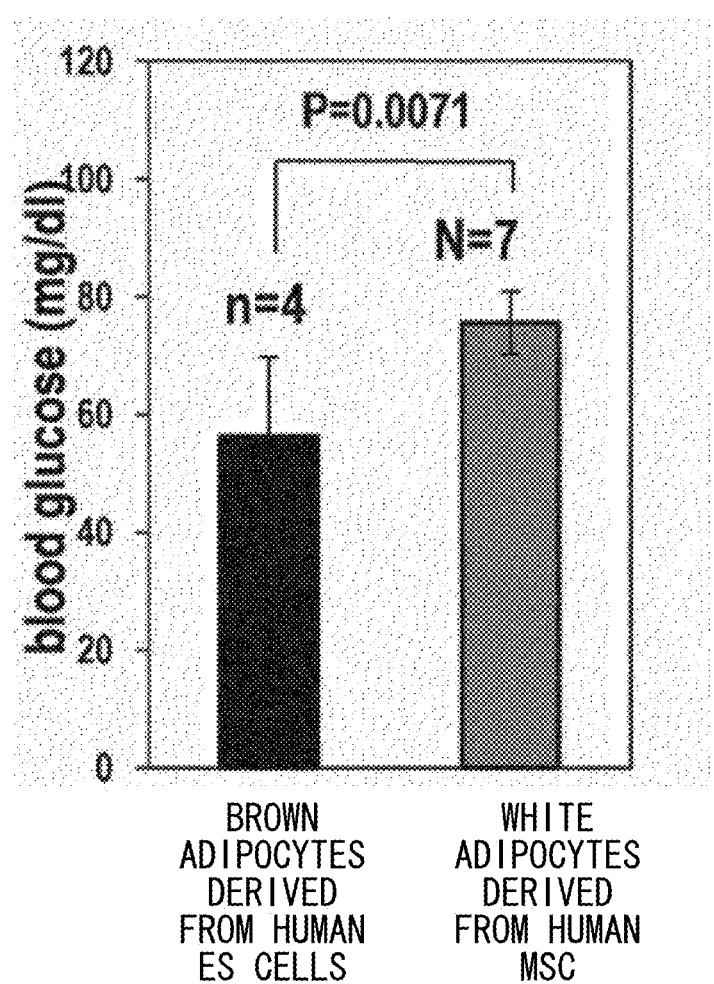
FIG. 14B is a graph showing fasting blood glucose levels in mice subcutaneously transplanted on the back with brown adipocytes differentiated from human ES cells.
Figure 14C:
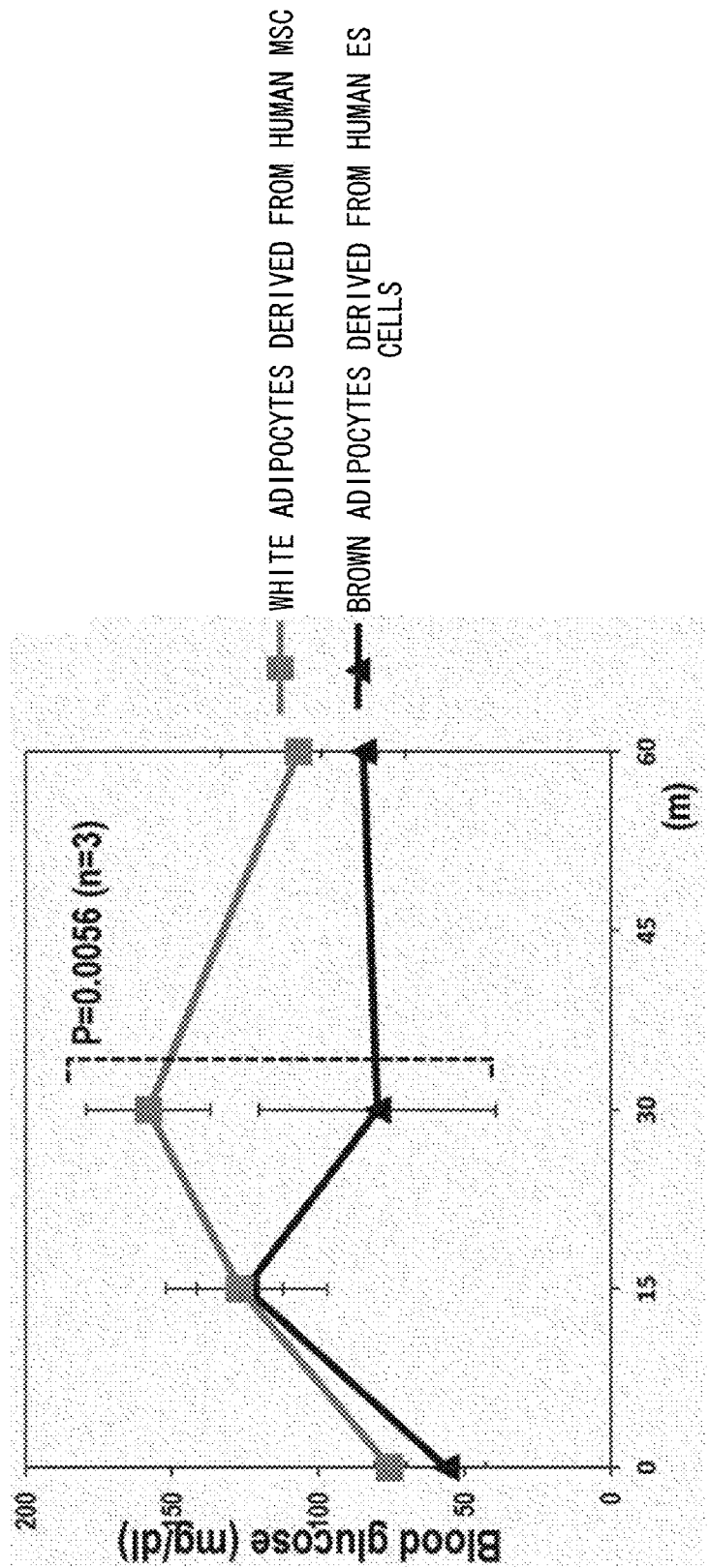
FIG. 14C is a graph showing the results of the glucose tolerance test of mice subcutaneously transplanted on the back with brown adipocytes differentiated from human ES cells.

The results, as shown in FIG. 14B, demonstrated that the fasting blood glucose level of the individual transplanted with human ES cell-derived brown adipocytes was significantly reduced compared to that of the individual transplanted with human MSC-derived white adipocytes. It was also confirmed, as shown in FIG. 14C, that the blood glucose level at 30 minutes after the glucose administration was significantly reduced in the individual transplanted with human ES cell-derived brown adipocytes compared to the individual transplanted with human MSC-derived white adipocytes.

Figure 14D:
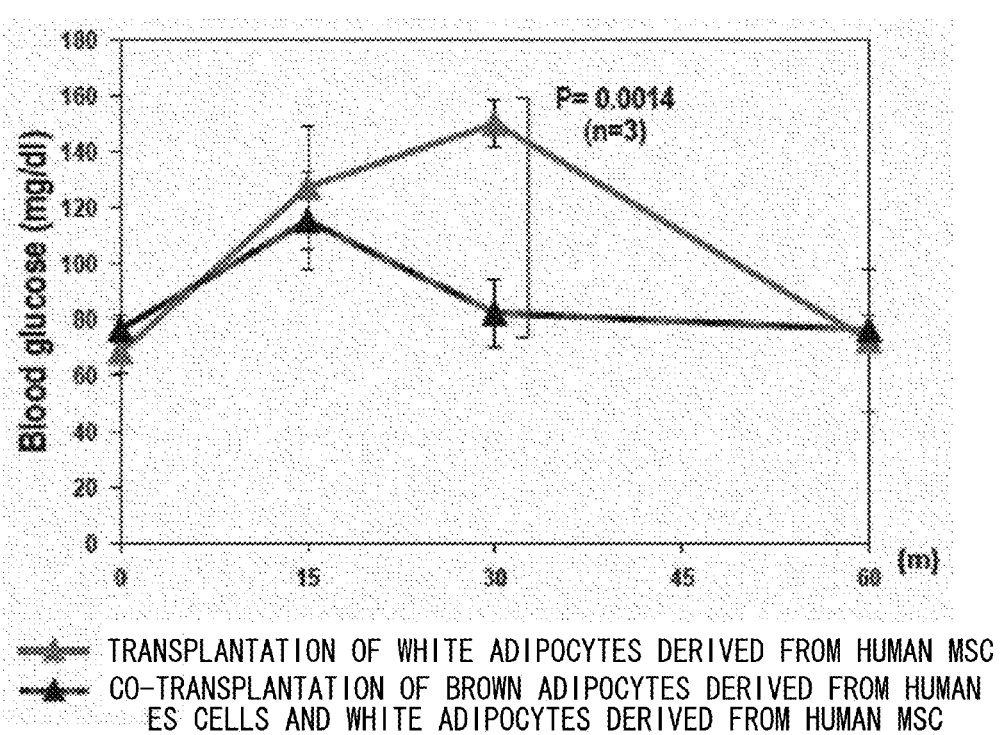
FIG. 14D is a graph showing the therapeutic effects on glucose metabolism disorder of mice subcutaneously transplanted on the back with brown adipocytes differentiated from human ES cells.

Furthermore, in order to investigate the therapeutic effect of the human pluripotent stem cell-derived brown adipocytes on glucose metabolism disorder associated with obesity, whether or not the glucose tolerance deteriorated by the transplantation of human MSC-derived white adipocytes is ameliorated by co-transplantation with human ES cell-derived brown adipocytes was investigated. As shown in FIG. 14D, it was proved that the raised blood glucose level of an individual transplanted with human MSC-derived white adipocytes at 30 minutes after the glucose administration was significantly reduced by co-transplantation of the same number ($1 \times 10^6$ cells) of human ES cell-derived brown adipocytes. That is, it was demonstrated that human ES cell-derived brown adipocytes show a significant therapeutic effect on abnormal glucose tolerance caused by human MSC-derived white adipocytes, i.e., glucose metabolism disorder associated with obesity.

As described above, though the fat metabolism-improving effect was recognized in both human ES cell-derived brown adipocytes and human MSC-derived white adipocytes, the glucose metabolism-improving effect was observed in the human ES cell-derived brown adipocytes only.

This glucose metabolism-improving effect is believed to be based on a possibility of direct uptake of blood glucose by human pluripotent stem cell-derived brown adipocytes, a possibility of activity of adipokines secreted by human pluripotent stem cell-derived brown adipocytes on other organs (such as liver, skeletal muscle, white adipocytes, or pancreatic β cells) to improve the glucose metabolism, or both possibilities.

Example 11

Confirmation of Non-Production of Active Oxygen in Brown Adipocytes Produced from Human Embryonic Stem Cells Brown adipocytes were differentiated from KhES-3 cell line in accordance with the method described in Example 5, and 200 μM of 2,7-dichlorodihydroflurescein diacetate (DCFDA), which is commonly used as a probe for intracellular active oxygen species, was added thereto. The generation of active oxygen species was evaluated by fluorescence microscopic observation. As a positive control, a similar experiment was carried out using human umbilical vein endothelial cells (HUVECs), which constitutively produce active oxygen species.

As a result, as shown in FIG. 15, though the signal of DCFDA which acquired fluorescent activity by intracellular active oxygen species was detected in HUVECs, the signal was not detected in human ES cell-derived brown adipocytes at all.

Thus, it was confirmed that human embryonic stem cell-derived brown adipocytes do not generate active oxygen species due to the high expression of UCP-1 by the cells. This fact strongly suggests the safety and the effectiveness of the use of human pluripotent stem cell-derived brown adipocytes in adipocyte transplantation therapy in coronary artery bypass surgery.

Example 12

Figure 16A:
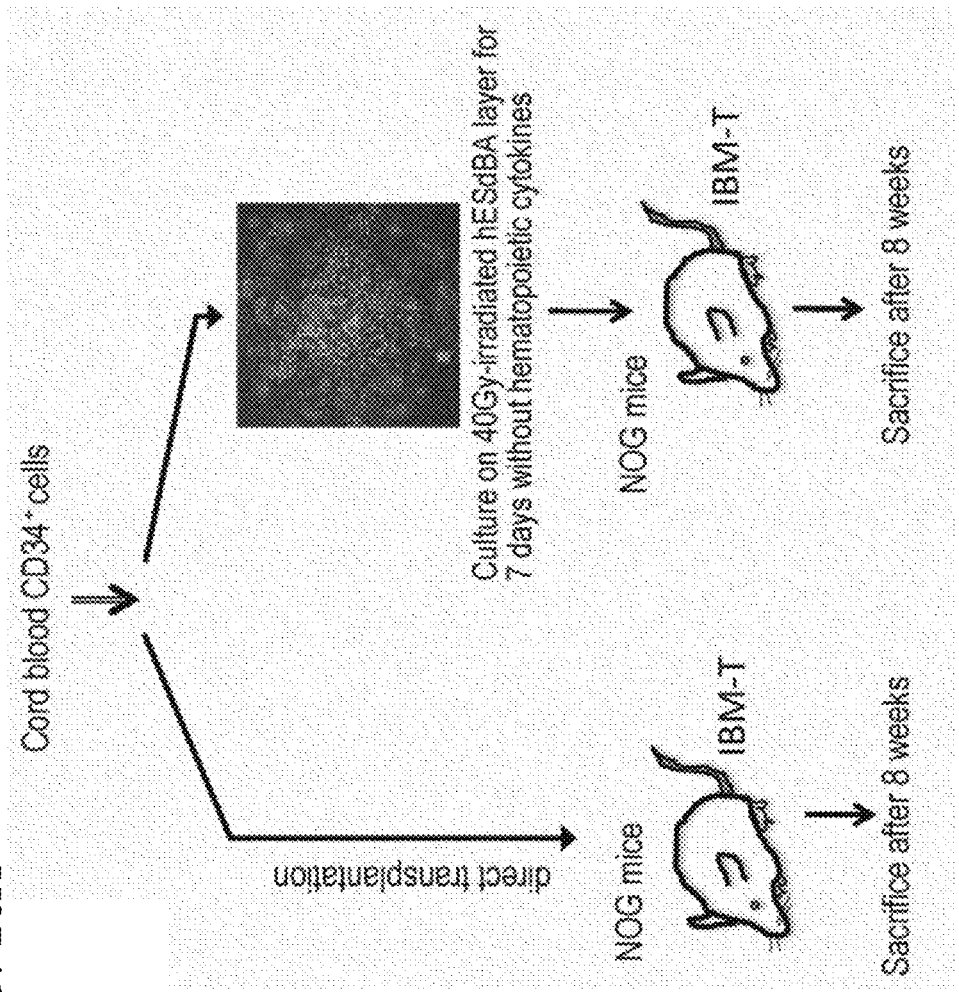
FIG. 16A is an explanatory drawing of a hematopoietic stromal function test of brown adipocytes differentiated from human ES cells.

Confirmation of Hematopoietic Stromal Function of Brown Adipocytes Produced from Human Embryonic Stem Cells Brown adipocytes were produced from human ES cells (KhES-3 cell line) using a culture plate having a diameter of 6 cm in accordance with the method described in Example 5. The hematopoiesis supporting ability of human ES cell-derived brown adipocytes was evaluated by the method described in FIG. 16A. Specifically, human ES cell-derived brown adipocytes were irradiated with γ-rays (40 Gy) to stop the proliferation. The medium was replaced by a 10% fetal calf serum-containing RPMI1640 medium (but not containing any recombinant cytokine at all), and then $6 \times 10^5$ human cord blood CD34 positive cells (hematopoietic stem/precursor cells) were cultured on the human ES cell-derived brown adipocytes. After 7 days, the floating cells were collected and were washed with physiological saline (saline) once. A suspension of the cells was produced at a concentration of $2 \times 10^5$ cells/10 μL (saline) and was transplanted into the thighbone bone marrow of each 6-week old female non-obese diabetic/severe combined immunodeficiency (NOD/SCID)/γc$^{null}$ (NOG) mouse. The intra-bone marrow transplantation was performed in accordance with a common method (the details are described in, for example, Non-Patent Literature 8). The mice were euthanized at 6 weeks, 8 weeks, or 12 weeks after the transplantation, and hematopoietic cells were collected from the bone marrow, the spleen, and the thymus. The chimerism rate (positive ratio of human blood cells in an individual mouse) was calculated by flow cytometry using a human specific CD45 antibody (pan-leukocyte marker), a human specific CD33 antibody (myeloid cell marker), a human specific CD19 antibody (B-cell marker), and a human specific CD3 antibody (T-cell marker). As a control, an experiment in which uncultured human cord blood CD34 positive cells were directly transplanted (hereinafter, referred to as direct transplantation) was also carried out.

Figure 16B:
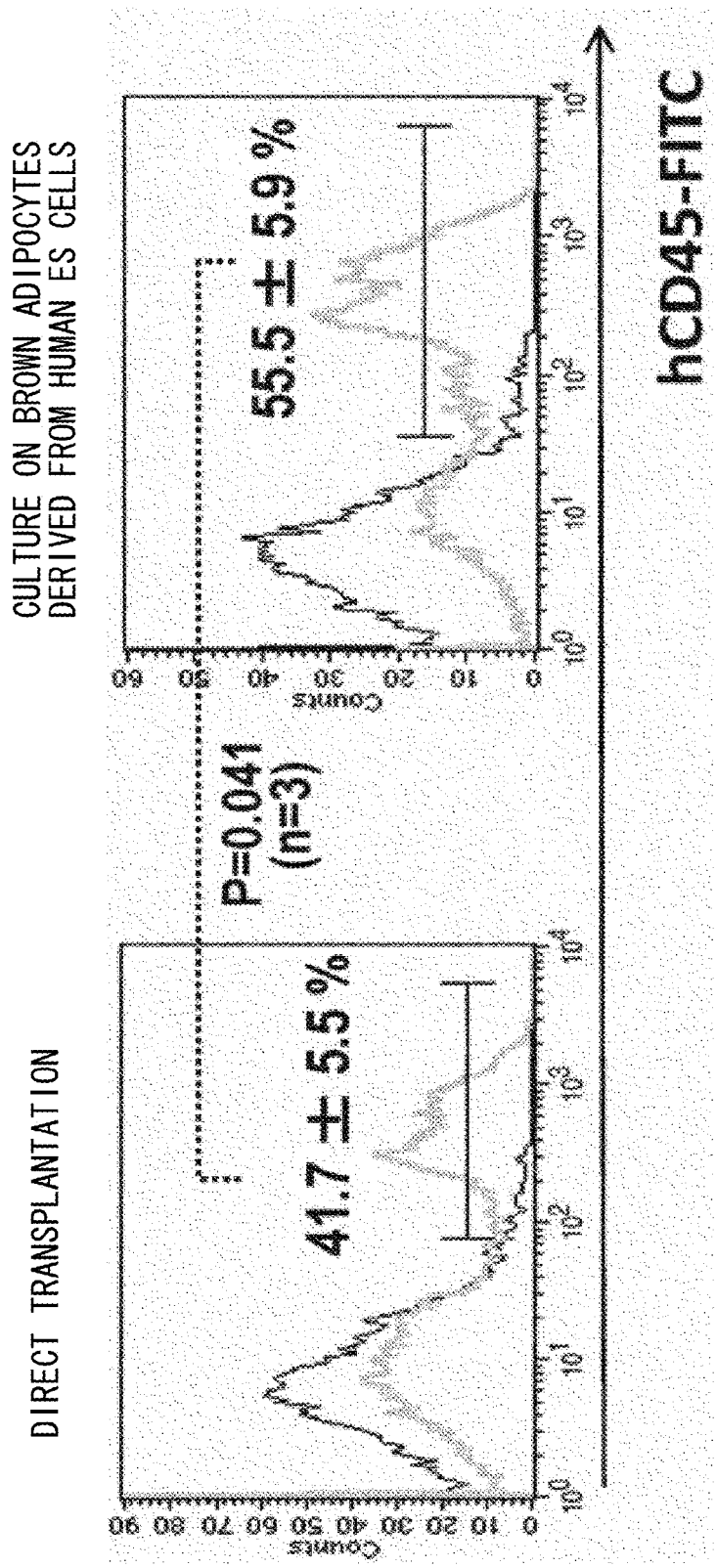
FIG. 16B includes graphs showing evaluation results of human CD45-expressing cells by FACS (registered trademark).
Figure 16C:
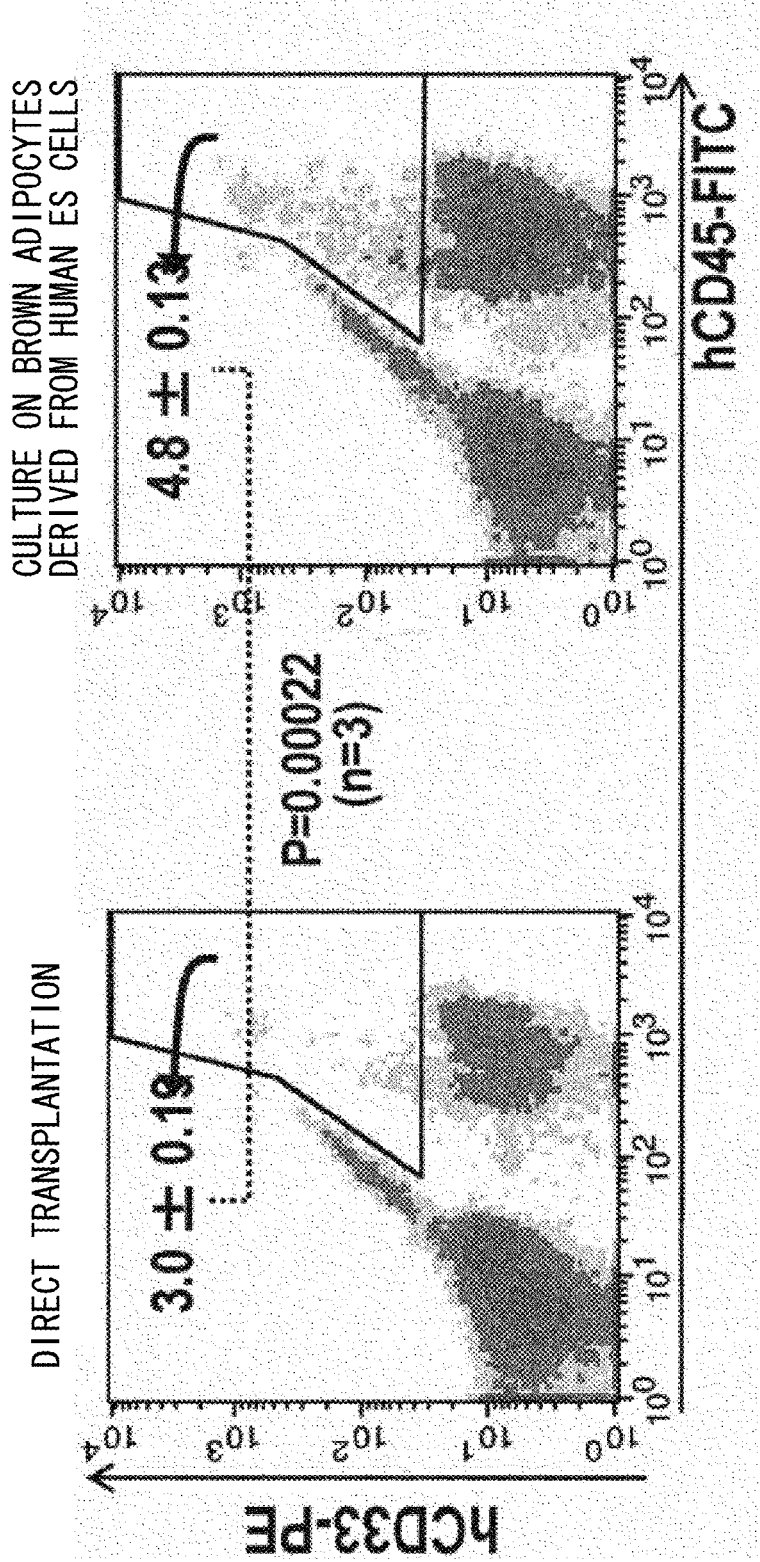
FIG. 16C includes graphs showing evaluation results of human CD33 and human CD45-expressing cells by FACS (registered trademark).

The results demonstrated that 1) the positive ratio of human CD45 positive cells in the spleen was significantly increased in the group of co-culture with human ES cell-derived brown adipocytes compared to the direct transplantation group (FIG. 16B) and 2) the positive ratio of human CD33 positive cells in the spleen was significantly increased in the group of co-culture with human ES cell-derived brown adipocytes compared to the direct transplantation group (FIG. 16C). This means that human ES cell-derived brown adipocytes function as stromas that support the proliferation and differentiation of myeloid hematopoietic precursor cells (precursor cells of granulocytes and macrophages).

Figure 16D:
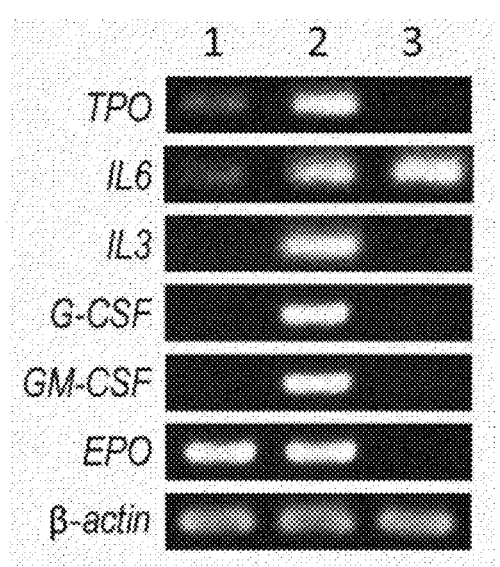
FIG. 16D includes photographs of electrophoresis showing evaluation results of hematopoietic cytokine expression of brown adipocytes differentiated from human ES cells.
Figure 16E:
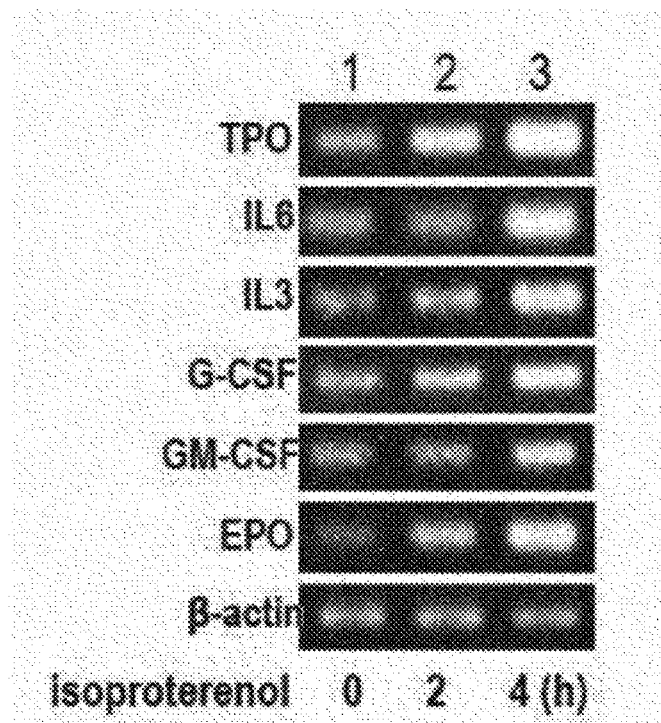
FIG. 16E includes photographs of electrophoresis showing the influence of a brown adipocyte stimulant on the hematopoietic cytokine expression levels of brown adipocytes differentiated from human ES cells.

The findings described above were also proved by the results of investigation of the expressions of cytokine genes in human ES cell-derived brown adipocytes. As shown in FIG. 16D, in human ES cell-derived brown adipocytes, many types of hematopoietic cytokines (thrombopoietin (TPO), IL6, IL3, granulocyte colony-stimulating factor (G-CSF), granulocyte/macrophage colony-stimulating factor (GM-CSF), and erythropoietin (EPO)) were expressed, whereas in human MSC-derived white adipocytes, only limited cytokines such as IL6 were expressed. In addition, as shown in FIG. 16E, it was confirmed that the expression levels of these cytokines (TPO, IL6, IL3, G-CSF, GM-CSF, and EPO) in human ES cell-derived brown adipocytes are increased by treatment with a brown adipocyte stimulant, isoproterenol.

Figure 16F:
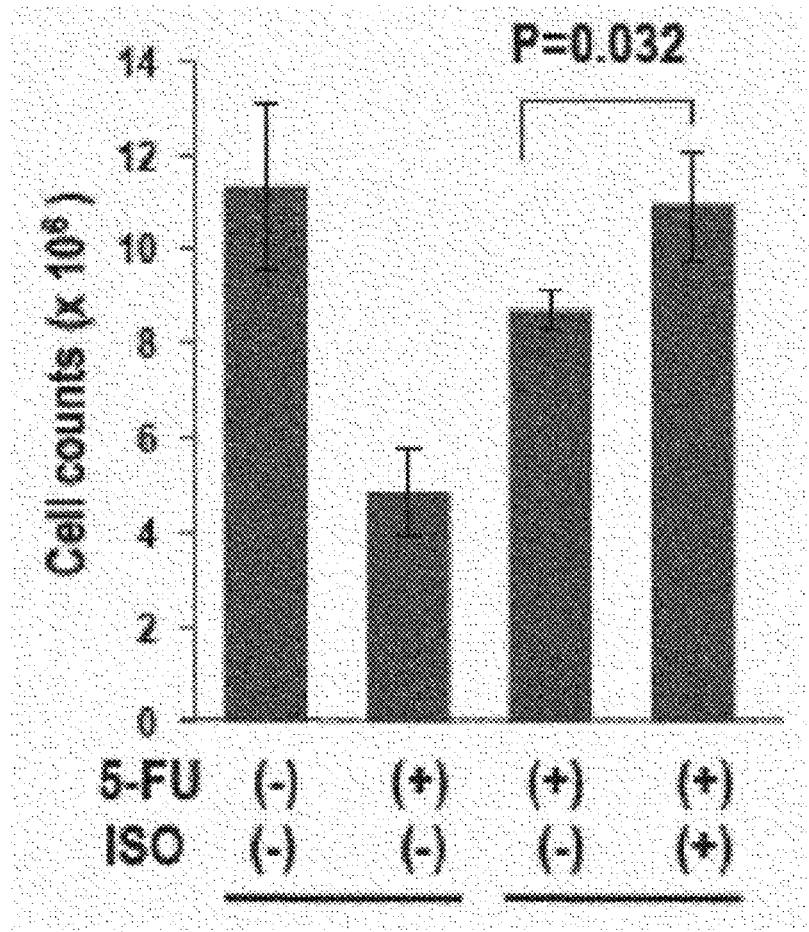
FIG. 16F is a graph showing the myelosuppression-relieving effect by a stimulant of brown adipocytes differentiated from human ES cells.

Furthermore, whether or not a brown adipocyte stimulant has an effect of relieving a severe side effect of anticancer drug administration, myelosuppression, was investigated. Specifically, an anticancer drug, 5-fluorouracil (5-FU), was administered to 10-week old mice (male, ICR strain) at a dose of 100 mg/kg. Isoproterenol (30 μmol/kg) or saline was administered to the mice on 3 to 6 days after the administration, and bone marrow cells were collected from the thighbone over time and were counted. The results, as shown in FIG. 16F, demonstrated that though myelosuppression was the highest on the 3rd day from the 5-FU administration, the number of bone marrow cells on the 7th day from the 5-FU administration was significantly increased in the mice administered with a brown adipocyte stimulant, isoproterenol (ISO) (P=0.032). That is, the results demonstrated that a brown adipocyte stimulant relieves myelosuppression associated with anticancer drug administration and enhances recovery from myelosuppression.

In conventional research on hematopoiesis-supporting cells, the object is only the niche (cell cluster contributing to stopping the cell cycle at the G0 phase and composed of immature osteoblasts and sinusoidal endothelial cells) of hematopoietic stem cells, and stromal cells contributing to support of hematopoiesis of "hematopoietic precursor cells committed to particular lineages" have not been studied at all. The above-described results show that brown adipocytes function as stromas of myeloid hematopoietic precursor cells. This means that human pluripotent stem cell-derived brown adipocytes are useful in cell therapy for shortening the period of hematopoietic disorder or myelosuppression (which causes a decrease in function of preventing infection to trigger severe infection such as sepsis) after anticancer treatment.

This effect of improving the hematopoietic function is believed to be caused by a possibility of direct intercellular interaction between human pluripotent stem cell-derived brown adipocytes and myeloid hematopoietic precursor cells, a possibility of an improvement in hematopoietic function by indirect action of adipokine secreted by human pluripotent stem cell-derived brown adipocytes on myeloid hematopoietic precursor cells, or both possibilities.

INDUSTRIAL APPLICABILITY

The present invention can stably supply human brown adipocytes that were not available until now and can thereby provide a tool for research for analyzing, for example, occurrence, differentiation, or dedifferentiation of human brown adipocytes, a tool for cell therapy of, for example, obesity, insulin resistance, or hyperlipidemia, a transplantation material for improving the results of coronary artery bypass surgery, and a tool for cell therapy of hematopoietic disorder or myelosuppression after anticancer drug administration. Furthermore, it is possible to provide a tool for research for searching brown adipocyte specific adipokine in order to develop novel internal therapy for obesity, insulin resistance, or hyperlipidemia, for an improvement in the result of coronary artery bypass surgery, and for hematopoietic disorder or myelosuppression after anticancer drug administration.

Human ES cells and human iPS cells, which are examples of the starting material of brown adipocytes according to the present invention, have infinite proliferation ability, and therefore are considerably easy to be stably produced at an industrial scale. In addition, brown adipocytes can be produced from human pluripotent stem cells within about 2 weeks and can be supplied according to need. The technology for producing the brown adipocytes can be performed using common cell culture facilities and therefore can be implemented in any country or area in all over the world. Accordingly, the technology can be expanded to huge plant industry, is practical, and has a high industrial value.

The invention claimed is:

1. A method of producing brown adipocytes, comprising the steps of:
   (a) providing mouse or human pluripotent stem cells,
   (b) culturing the pluripotent stem cells of step (a) in a serum-free non-adhesive culture in the presence of BMP4, VEGF, SCF, Flt3L, IL6 and IGF2 to form cell aggregates; and
   (c) differentiating the cell aggregates of step (b) in an adhesive culture in the presence of BMP7, VEGF, SCF, Flt3L, IL6 and IGF3 to obtain brown adipocytes.

2. The method according to claim 1, wherein the pluripotent stem cells are ES cells or iPS cells.

3. The method according to claim 2, wherein the iPS cells are established using Sendai virus vectors encoding Oct3/4, Sox2, Klf4 and Myc.

4. The method according to claim 1, wherein the pluripotent stem cells are human pluripotent stem cells.

* * * * *

```
                              SEQUENCE LISTING

<160> NUMBER OF SEQ ID NOS: 32

<210> SEQ ID NO 1
<211> LENGTH: 22
<212> TYPE: DNA
<213> ORGANISM: Unknown
<220> FEATURE:
<223> OTHER INFORMATION: Synthetic

<400> SEQUENCE: 1
cccgaaagag aaagcgaacc ag                                               22

<210> SEQ ID NO 2
<211> LENGTH: 20
<212> TYPE: DNA
<213> ORGANISM: Unknown
<220> FEATURE:
<223> OTHER INFORMATION: Synthetic

<400> SEQUENCE: 2
aatgtatcga aggtgctcaa                                                  20

<210> SEQ ID NO 3
<211> LENGTH: 22
<212> TYPE: DNA
<213> ORGANISM: Unknown
<220> FEATURE:
<223> OTHER INFORMATION: Synthetic

<400> SEQUENCE: 3
acaagagaaa aaacatgtat gg                                               22

<210> SEQ ID NO 4
<211> LENGTH: 27
<212> TYPE: DNA
<213> ORGANISM: Unknown
<220> FEATURE:
<223> OTHER INFORMATION: Synthetic

<400> SEQUENCE: 4
atgcgctggt tcacgcccgc gcccagg                                          27

<210> SEQ ID NO 5
<211> LENGTH: 22
<212> TYPE: DNA
<213> ORGANISM: Unknown
<220> FEATURE:
```

<223> OTHER INFORMATION: Synthetic

<400> SEQUENCE: 5
acaagagaaa aaacatgtat gg                                                22

<210> SEQ ID NO 6
<211> LENGTH: 25
<212> TYPE: DNA
<213> ORGANISM: Unknown
<220> FEATURE:
<223> OTHER INFORMATION: Synthetic

<400> SEQUENCE: 6
cgcgctggca gggccgctgc tcgac                                             25

<210> SEQ ID NO 7
<211> LENGTH: 22
<212> TYPE: DNA
<213> ORGANISM: Unknown
<220> FEATURE:
<223> OTHER INFORMATION: Synthetic

<400> SEQUENCE: 7
taactgacta gcaggcttgt cg                                                22

<210> SEQ ID NO 8
<211> LENGTH: 26
<212> TYPE: DNA
<213> ORGANISM: Unknown
<220> FEATURE:
<223> OTHER INFORMATION: Synthetic

<400> SEQUENCE: 8
tccacataca gtcctggatg atgatg                                            26

<210> SEQ ID NO 9
<211> LENGTH: 22
<212> TYPE: DNA
<213> ORGANISM: Unknown
<220> FEATURE:
<223> OTHER INFORMATION: Synthetic

<400> SEQUENCE: 9
ggatcactag gtgatatcga gc                                                22

<210> SEQ ID NO 10
<211> LENGTH: 29
<212> TYPE: DNA
<213> ORGANISM: Unknown
<220> FEATURE:
<223> OTHER INFORMATION: Synthetic

<400> SEQUENCE: 10
accagacaag agtttaagag atatgtatc                                         29

<210> SEQ ID NO 11
<211> LENGTH: 20
<212> TYPE: DNA
<213> ORGANISM: Unknown
<220> FEATURE:
<223> OTHER INFORMATION: Synthetic

<400> SEQUENCE: 11
tctctcagga tcggcctcta                                                   20

```
<210> SEQ ID NO 12
<211> LENGTH: 20
<212> TYPE: DNA
<213> ORGANISM: Unknown
<220> FEATURE:
<223> OTHER INFORMATION: Synthetic

<400> SEQUENCE: 12
ccgtgtagcg aggtttgatt                                               20

<210> SEQ ID NO 13
<211> LENGTH: 20
<212> TYPE: DNA
<213> ORGANISM: Unknown
<220> FEATURE:
<223> OTHER INFORMATION: Synthetic

<400> SEQUENCE: 13
gcggtctgtt agctttggag                                               20

<210> SEQ ID NO 14
<211> LENGTH: 20
<212> TYPE: DNA
<213> ORGANISM: Unknown
<220> FEATURE:
<223> OTHER INFORMATION: Synthetic

<400> SEQUENCE: 14
agtgtcttcg gaaagggaca                                               20

<210> SEQ ID NO 15
<211> LENGTH: 20
<212> TYPE: DNA
<213> ORGANISM: Unknown
<220> FEATURE:
<223> OTHER INFORMATION: Synthetic

<400> SEQUENCE: 15
cggaacgtga aggccaccat                                               20

<210> SEQ ID NO 16
<211> LENGTH: 20
<212> TYPE: DNA
<213> ORGANISM: Unknown
<220> FEATURE:
<223> OTHER INFORMATION: Synthetic

<400> SEQUENCE: 16
ccctatccac acgtgaacct                                               20

<210> SEQ ID NO 17
<211> LENGTH: 20
<212> TYPE: DNA
<213> ORGANISM: Unknown
<220> FEATURE:
<223> OTHER INFORMATION: Synthetic

<400> SEQUENCE: 17
tctcttcctt ggaccacacc                                               20

<210> SEQ ID NO 18
<211> LENGTH: 20
<212> TYPE: DNA
<213> ORGANISM: Unknown
<220> FEATURE:
<223> OTHER INFORMATION: Synthetic
```

```
<400> SEQUENCE: 18
cagcctcact gttggggtat                                              20

<210> SEQ ID NO 19
<211> LENGTH: 20
<212> TYPE: DNA
<213> ORGANISM: Unknown
<220> FEATURE:
<223> OTHER INFORMATION: Synthetic

<400> SEQUENCE: 19
cactggtacc accacagcac                                              20

<210> SEQ ID NO 20
<211> LENGTH: 20
<212> TYPE: DNA
<213> ORGANISM: Unknown
<220> FEATURE:
<223> OTHER INFORMATION: Synthetic

<400> SEQUENCE: 20
atcctgcctc cacatgtacg                                              20

<210> SEQ ID NO 21
<211> LENGTH: 20
<212> TYPE: DNA
<213> ORGANISM: Unknown
<220> FEATURE:
<223> OTHER INFORMATION: Synthetic

<400> SEQUENCE: 21
gtgaagacca gcctctttgc                                              20

<210> SEQ ID NO 22
<211> LENGTH: 20
<212> TYPE: DNA
<213> ORGANISM: Unknown
<220> FEATURE:
<223> OTHER INFORMATION: Synthetic

<400> SEQUENCE: 22
aatccgtctt catccacagg                                              20

<210> SEQ ID NO 23
<211> LENGTH: 20
<212> TYPE: DNA
<213> ORGANISM: Unknown
<220> FEATURE:
<223> OTHER INFORMATION: Synthetic

<400> SEQUENCE: 23
agcctcaccc tctgcagtta                                              20

<210> SEQ ID NO 24
<211> LENGTH: 20
<212> TYPE: DNA
<213> ORGANISM: Unknown
<220> FEATURE:
<223> OTHER INFORMATION: Synthetic

<400> SEQUENCE: 24
aggtggtggc atcagtcttc                                              20

<210> SEQ ID NO 25
<211> LENGTH: 20
```

```
<212> TYPE: DNA
<213> ORGANISM: Unknown
<220> FEATURE:
<223> OTHER INFORMATION: Synthetic

<400> SEQUENCE: 25
tggcatacag ctcacagctc                                                     20

<210> SEQ ID NO 26
<211> LENGTH: 20
<212> TYPE: DNA
<213> ORGANISM: Unknown
<220> FEATURE:
<223> OTHER INFORMATION: Synthetic

<400> SEQUENCE: 26
agacacccgg tccttaaacc                                                     20

<210> SEQ ID NO 27
<211> LENGTH: 20
<212> TYPE: DNA
<213> ORGANISM: Unknown
<220> FEATURE:
<223> OTHER INFORMATION: Syhtnetic

<400> SEQUENCE: 27
gaccactccc actcctttga                                                     20

<210> SEQ ID NO 28
<211> LENGTH: 20
<212> TYPE: DNA
<213> ORGANISM: Unknown
<220> FEATURE:
<223> OTHER INFORMATION: Synthetic

<400> SEQUENCE: 28
gatgcaggct ccactttgat                                                     20

<210> SEQ ID NO 29
<211> LENGTH: 20
<212> TYPE: DNA
<213> ORGANISM: Unknown
<220> FEATURE:
<223> OTHER INFORMATION: Synthetic

<400> SEQUENCE: 29
ctggggagct tcacaaacat                                                     20

<210> SEQ ID NO 30
<211> LENGTH: 20
<212> TYPE: DNA
<213> ORGANISM: Unknown
<220> FEATURE:
<223> OTHER INFORMATION: Synthetic

<400> SEQUENCE: 30
ccacagctct gggtttgatt                                                     20

<210> SEQ ID NO 31
<211> LENGTH: 19
<212> TYPE: DNA
<213> ORGANISM: Unknown
<220> FEATURE:
<223> OTHER INFORMATION: Syhtetic

<400> SEQUENCE: 31
```

```
tccatggaag aagccatca                                                    19

<210> SEQ ID NO 32
<211> LENGTH: 20
<212> TYPE: DNA
<213> ORGANISM: Unknown
<220> FEATURE:
<223> OTHER INFORMATION: Synthetic

<400> SEQUENCE: 32
tggcagtgac atgtggtctc                                                   20
```